(12) United States Patent
Horava et al.

(10) Patent No.: US 11,109,865 B1
(45) Date of Patent: Sep. 7, 2021

(54) NERVE REPAIR DEVICE AND METHOD OF USE

(71) Applicant: Triton Systems, Inc., Chelmsford, MA (US)

(72) Inventors: Sarena Horava, Medway, MA (US); Yoojeong Kim, Sudbury, MA (US); Anant Singh, Woburn, MA (US)

(73) Assignee: TRITON SYSTEMS, INC., Chelmsford, MA (US)

( * ) Notice: Subject to any disclaimer, the term of this patent is extended or adjusted under 35 U.S.C. 154(b) by 27 days.

(21) Appl. No.: 16/042,413

(22) Filed: Jul. 23, 2018

Related U.S. Application Data

(60) Provisional application No. 62/535,570, filed on Jul. 21, 2017, provisional application No. 62/570,421, filed on Oct. 10, 2017.

(51) Int. Cl.
*A61B 17/11* (2006.01)
*A61B 17/00* (2006.01)
(Continued)

(52) U.S. Cl.
CPC . *A61B 17/1128* (2013.01); *A61B 2017/00004* (2013.01); *A61K 35/30* (2013.01);
(Continued)

(58) Field of Classification Search
CPC .............. A61B 17/1128; A61B 17/112; A61B 17/1125; A61B 2017/1125;
(Continued)

(56) References Cited

U.S. PATENT DOCUMENTS 3,786,817 A * 1/1974 Palma ................ A61B 17/1128
606/152
3,916,905 A * 11/1975 Kuhn ................ A61B 17/1128
606/152
(Continued)

FOREIGN PATENT DOCUMENTS

WO 2012161823 A1 11/2012

OTHER PUBLICATIONS

Sullivan et al., "Insulin-like Growth Factors in the Peripheral Nervous System".*
(Continued)

*Primary Examiner* — Darwin P Erezo
*Assistant Examiner* — Brigid K Byrd
(74) *Attorney, Agent, or Firm* — Troutman Pepper Hamilton Sanders LLP

(57) ABSTRACT

A device may include a shaft with a dispensing channel, an evacuating channel, a proximal end, and a distal end. The device may further include an enclosure attached to the distal portion of the shaft, the enclosure having a first portion and a second portion that form a bore when the enclosure is closed. The device may further include a handle attached to the proximal end of the shaft, which is configured to open and close the enclosure. A method of delivering a solution to a nerve repair site may include obtaining such a device, closing its enclosure around the nerve repair site, delivering one or more solutions through the dispensing channel to the nerve repair site, removing one or more solutions through the evacuating channel from the nerve repair site, and opening the enclosure to remove it from the nerve repair site.

19 Claims, 39 Drawing Sheets

(51) Int. Cl.
*A61L 27/38* (2006.01)
*A61K 35/30* (2015.01)
*A61L 27/36* (2006.01)

(52) U.S. Cl.
CPC .......... *A61L 27/3675* (2013.01); *A61L 27/383* (2013.01); *A61L 27/3878* (2013.01); *A61L 2430/32* (2013.01)

(58) Field of Classification Search
CPC .......... A61B 2017/00004; A61B 17/11; A61B 17/29; A61B 17/08; A61K 35/30; A61L 27/3675; A61L 27/383; A61L 27/3878
See application file for complete search history.

(56) References Cited

U.S. PATENT DOCUMENTS

| | | | | |
|---|---|---|---|---|
| 4,306,561 | A * | 12/1981 | de Medinaceli ... | A61B 17/1128 606/152 |
| 9,955,973 | B2 * | 5/2018 | Winograd .......... | A61B 17/1128 |
| 2004/0138649 | A1 * | 7/2004 | Takamoto ............ | A61B 17/11 606/1 |
| 2004/0199187 | A1 * | 10/2004 | Loughran ................ | A61F 2/04 606/152 |
| 2006/0085031 | A1 * | 4/2006 | Bettuchi ............... | A61B 17/08 606/215 |
| 2012/0078293 | A1 * | 3/2012 | Hassidov ............ | A61L 26/0076 606/213 |
| 2013/0053942 | A1 * | 2/2013 | Kamel ...................... | A61F 2/95 623/1.11 |
| 2015/0190134 | A1 * | 7/2015 | Weisshaupt .......... | A61B 18/082 606/41 |

OTHER PUBLICATIONS

Zhang et al., "Erythropoietin attenuates propofol-induced hippocampal neuronal cell injury in developing rats by inhibiting toll-like receptor 4 expression", Neuroscience Letters, Jan. 2018 (Year: 2018).*
Davis et al., "Platelet-derived growth factors and fibroblast growth factors are mitogens for rat Schwann cells".*
Burdick et al., "Stimulation of neurite outgrowth by neurotrophins delivered from degradable hydrogels" 2006, Biomaterials (Year: 2006).*
Bittner, G. D. et al. The curious ability of polyethylene glycol fusion technologies to restore lost behaviors after nerve severance. J. Neurosci. Res. 94, 207-230 (2016).
Grinsell, D., Keating, C. P., Grinsell, D. & Keating, C. R Peripheral Nerve Reconstruction after Injury: A Review of Clinical and Experimental Therapies. Biomed Res. Int. 2014, 1-13 (2014).
Bittner, G. D. et al. Rapid, effective, and long-lasting behavioral recovery produced by microsutures, methylene blue, and polyethylene glycol after completely cutting rat sciatic nerves. J. Neurosci. Res. 90, 967-980 (2012).
Campbell, W. W. Evaluation and management of peripheral nerve injury. Clin. Neurophysiol. 119, 1951-1965 (2008).
Gaudet, A. D., Popovich, P. G. & Ramer, M. S. Wallerian degeneration: gaining perspective on inflammatory events after peripheral nerve injury. J. Neurotrauma 8, 110 (2011).
Sulaiman, W. & Dreesen, T. D. Effect of local application of transforming growth factor-beta at the nerve repair site following chronic axotomy and denervation on the expression of regeneration-associated genes. J. Neurosurg. 121, 359-874 (2014).
Evriviades, D. et al. Shaping the military wound: issues surrounding the reconstruction of injured servicemen at the Royal Centre for Defence Medicine. Philos. Trans. R. Soc. London B Biol. Sci. 366, 219-230 (2011).
Riley, D. C. et al. Polyethylene glycol-fused allografts produce rapid behavioral recovery after ablation of sciatic nerve segments. J. Neurosci. Res. 93, 572-83 (2015).
Ghergherehchi, C. L. et al. Effects of extracellular calcium and surgical techniques on restoration of axonal continuity by polyethylene glycol fusion following complete cut or crush severance of rat sciatic nerves. J. Neurosci. Res. 94, 231-245 (2016).
Britt, J. M. et al. Polyethylene Glycol Rapidly Restores Axonal Integrity and Improves the Rate of Motor Behavior Recovery After Sciatic Nerve Crush Injury. J. Neurophysiol. 104, 695-703 (2010).
Wood, M. D. et al. Affinity-based release of glial-derived neurotrophic factor from fibrin matrices enhances sciatic nerve regeneration. Acta Biomater. 5, 959-68 (2009).
Wood, M. D. et al. Fibrin matrices with affinity-based delivery systems and neurotrophic factors promote functional nerve regeneration. Biotechnol. Bioeng. 106, 970-9 (2010).
Marquardt, L. M. et al. Finely Tuned Temporal and Spatial Delivery of GDNF Promotes Enhanced Nerve Regeneration in a Long Nerve Defect Model. Tissue Eng. Part A 21, 2852-64 (2015).
Elfar, J. C., Jacobson, J. A., Puzas, J. E., Rosier, R. N. & Zuscik, M. J. Erythropoietin accelerates functional recovery after peripheral nerve injury. J. Bone Joint Surg. Am. 90, 1644-53 (2008).
Sundem, L. et al. Erythropoietin Enhanced Recovery After Traumatic Nerve Injury: Myelination and Localized Effects. J. Hand Surg. Am. 41, 999-1010 (2016).
Campana, W. M. et al. Erythropoietin reduces Schwann cell TNF-alpha, Wallerian degeneration and pain-related behaviors after peripheral nerve injury. Eur. J. Neurosci. 23, 617-26 (2006).
Yin, Z.-S., Zhang, H., Bo, W. & Gao, W. Erythropoietin promotes functional recovery and enhances nerve regeneration after peripheral nerve injury in rats. AJNR. Am. J. Neuroradiol. 31, 509-15 (2010).

* cited by examiner

NERVE REPAIR DEVICE AND METHOD OF USE

CROSS-REFERENCE TO RELATED APPLICATIONS

This application claims priority to and benefit of U.S. Provisional Application Ser. No. 62/535,570, filed Jul. 21, 2017, entitled "Nerve Repair Device and Method of Use," and U.S. Provisional Application Ser. No. 62/570,421, filed Oct. 10, 2017, entitled "Nerve Repair Device and Method of Use," each of which is hereby incorporated herein by reference in its entirety.

GOVERNMENT INTERESTS

The invention disclosed herein was developed with partial funding from the U.S. Government under Contract W81XWH-17-C-0076.

BACKGROUND

Within hours of a peripheral nerve injury (PNI), the severed axonal ends seal off to prevent the loss of cytoplasm and the influx of toxins. Surviving peripheral nerve axons (PNAs) naturally regenerate by the slow process of axonal outgrowths (about 1 mm/day) from the proximal ends. Additionally, severed distal segments begin to degenerate and fragment by Wallerian degeneration. Wallerian degeneration begins within 1-3 days post-injury, and distal segments are unable to generate action potentials within 3 days. By 6-8 weeks post-injury, the distal stump is comprised of only endoneurial tubes lined by Schwann cells. The Schwann cells involute and disappear if axonal regeneration does not occur. Endoneurial tubes that do not receive regenerating axons shrink, and are eventually obliterated by scar tissue. Muscle fibrosis and atrophy begin immediately after denervation, plateauing after 4 months at about 60-80% muscle loss. If satisfactory reinnervation is not timely, irreversible end-organ dysfunction follows.

Current clinical methods for repairing PNIs include microsutures, autologous nerve autografts, and synthetic or autologous conduits. However, these methods have had limited success that depends upon a number of factors, such as the mechanism of injury, the timing of the repair, the injury distance to target, the length of the nerve damage or gap, the type of nerve involved (e.g. motor, sensory, or mixed), and the surgeon's technique. Current technologies for nerve repair rely on proximal nerve regrowth to make the appropriate connections. Additionally, such methods do not limit cell-body death or Wallerian degeneration, which immediately decreases the pool of surviving neurons available. As a result, potential innervation of distal motor and sensory targets takes months to years, during which the muscles also lose capacity to reinnervate.

Due to the poor success of current clinical methods, numerous researched efforts have aimed to enhance axonal regeneration or decrease environmental inflammation through therapeutics. One alternative repair method is poly (ethylene glycol) (PEG) fusion, which has shown the potential to rapidly and effectively repair traumatically injured peripheral nerves. PEG-fusion connects severed nerve ends by using hybrid cell fusion to artificially fuse mammalian axons after injury to restore axonal continuity and prevent Wallerian degeneration. During PEG-fusion, a series of solutions and pharmaceutical agents are applied directly to the nerve at the microsutured repair site. Another approach to promote neuronal survival and axon outgrowth requires growth factors, such as nerve growth factor and glial cell-derived neurotropic factor, to be locally administered. Erythropoietin has been extensively studied to enhance functional recovery after peripheral nerve injury by protecting the injured nerve and reducing Wallerian degeneration. For these nerve repair approaches, there exists a need for a device that can deliver a solution or pharmaceutical agent locally to the nerve, isolating the solution to the appropriate nerve segment surrounding the nerve repair site.

SUMMARY

The instant disclosure relates generally to a nerve repair device and method of use. In one embodiment, a device may comprise a shaft comprising a dispensing channel and an evacuating channel, the shaft having a proximal end and a distal end; an enclosure attached to the distal end of the shaft, the enclosure having a first portion and a second portion, wherein the first portion and the second portion form a bore when the enclosure is closed; and a handle attached to the proximal end of the shaft and configured to open and close the enclosure.

In another embodiment, a method may comprise obtaining such a device; closing the enclosure around a nerve repair site, such that the nerve repair site occupies the bore of the enclosure; delivering a solution through the dispensing channel to the nerve repair site; removing the solution through the evacuating channel from the nerve repair site; and opening the enclosure to remove it from the nerve repair site.

Further embodiments of the instant disclosure are described herein.

DETAILED DESCRIPTION

Figure 1:
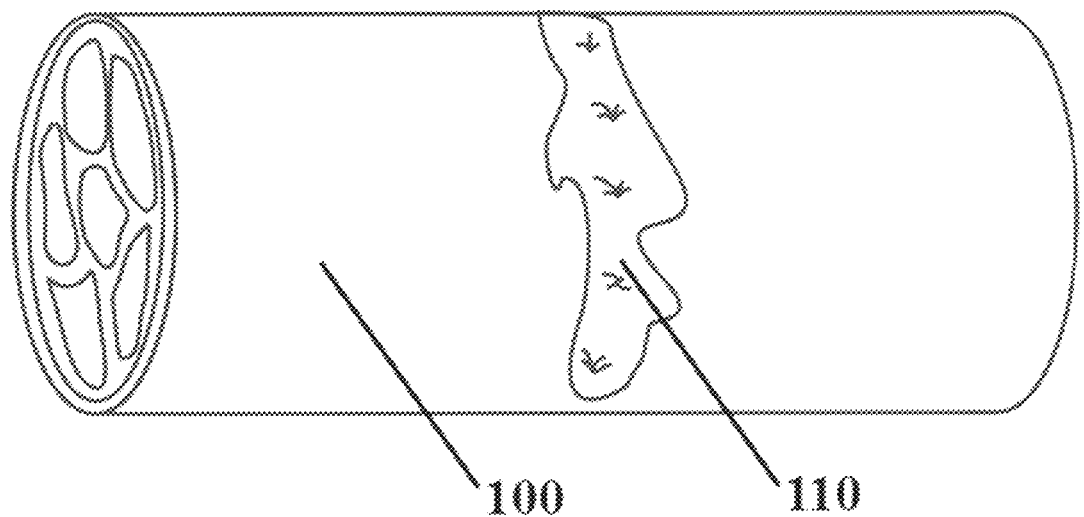
FIG. 1 illustrates a schematic of a nerve repair site, in accordance with the instant disclosure.

This disclosure is not limited to the particular systems, devices and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to an "agent" is a reference to one or more agents and equivalents thereof known to those skilled in the art, and so forth.

As used herein, the term "about" means plus or minus 10% of the numerical value of the number with which it is being used. Therefore, about 50 mm means in the range of 45 mm to 55 mm.

As used herein, the term "consists of" or "consisting of" means that the device or method includes only the elements, steps, or ingredients specifically recited in the particular claimed embodiment or claim.

In embodiments or claims where the term "comprising" is used as the transition phrase, such embodiments can also be envisioned with replacement of the term "comprising" with the terms "consisting of" or "consisting essentially of."

As used herein, the term "biocompatible" refers to non-harmful compatibility with living tissue. Biocompatibility is a broad term that describes a number of materials, including bioinert materials, bioactive materials, bioabsorbable materials, biostable materials, biotolerant materials, or any combination thereof. Similarly, the term "non-neurotoxic" refers to a lack of toxicity to nerve tissue.

A "therapeutically effective amount" or "effective amount" of a composition or solution is a predetermined amount calculated to achieve the desired effect, i.e., to ease, inhibit, block, heal, or reverse a disorder. The activity contemplated by the present methods includes both medical therapeutic and/or prophylactic treatment, as appropriate. The specific dose of a compound or solution administered according to this invention to obtain therapeutic and/or prophylactic effects will, of course, be determined by the particular circumstances surrounding the case, including, for example, the compound administered, the route of administration, and the condition being treated. The effective amount administered will be determined by the physician in the light of the relevant circumstances including the condition to be treated and the choice of compound to be administered. A therapeutically effective amount of compound of this invention is typically an amount such that when it is administered in a physiologically tolerable excipient composition or solution, it is sufficient to achieve an effective systemic concentration or local concentration in the tissue.

Device

The instant disclosure is directed to a nerve repair device and method of use. Such devices and methods may be applied to the site of the repair, a schematic of which is illustrated in FIG. 1. In one embodiment, a device 200 may comprise a shaft 210 having a proximal end and a distal end. In some embodiments the shaft may be flexible, and in other embodiments the shaft may be rigid. In certain embodiments, the shaft may be a combination of flexible and rigid. In one embodiment, for example, the shaft may be substantially flexible at the proximal end and substantially rigid or semi-rigid at the distal end. In another embodiment, for example, the shaft may be substantially flexible at the distal end and substantially rigid or semi-rigid at the proximal end. In certain embodiments, the shaft may comprise a biocompatible metal, a biocompatible plastic, a biocompatible glass, or any combination thereof. In some embodiments, the shaft may have a length from about 1 cm to about 100 cm. The length of the shaft may be, for example, about 1 cm, about 5 cm, about 10 cm, about 15 cm, about 20 cm, about 25 cm, about 30 cm, about 35 cm, about 40 cm, about 45 cm, about 50 cm, about 55 cm, about 60 cm, about 65 cm, about 70 cm, about 75 cm, about 80 cm, about 85 cm, about 90 cm, about 95 cm, about 100 cm, from about 5 cm to about 30 cm, from about 5 cm to about 50 cm, from about 10 cm to about 30 cm, or any range between any two of these values, including endpoints.

Figure 2:
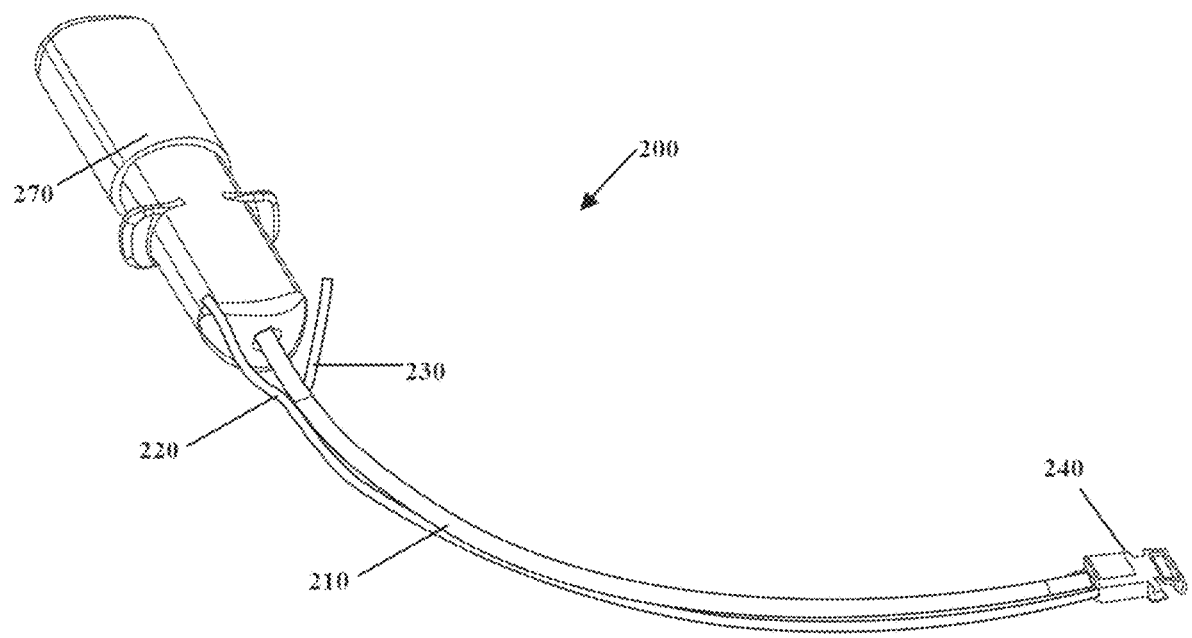
FIG. 2 illustrates an embodiment of a device having a handle, a shaft, and an enclosure in accordance with the instant disclosure.
Figure 6:
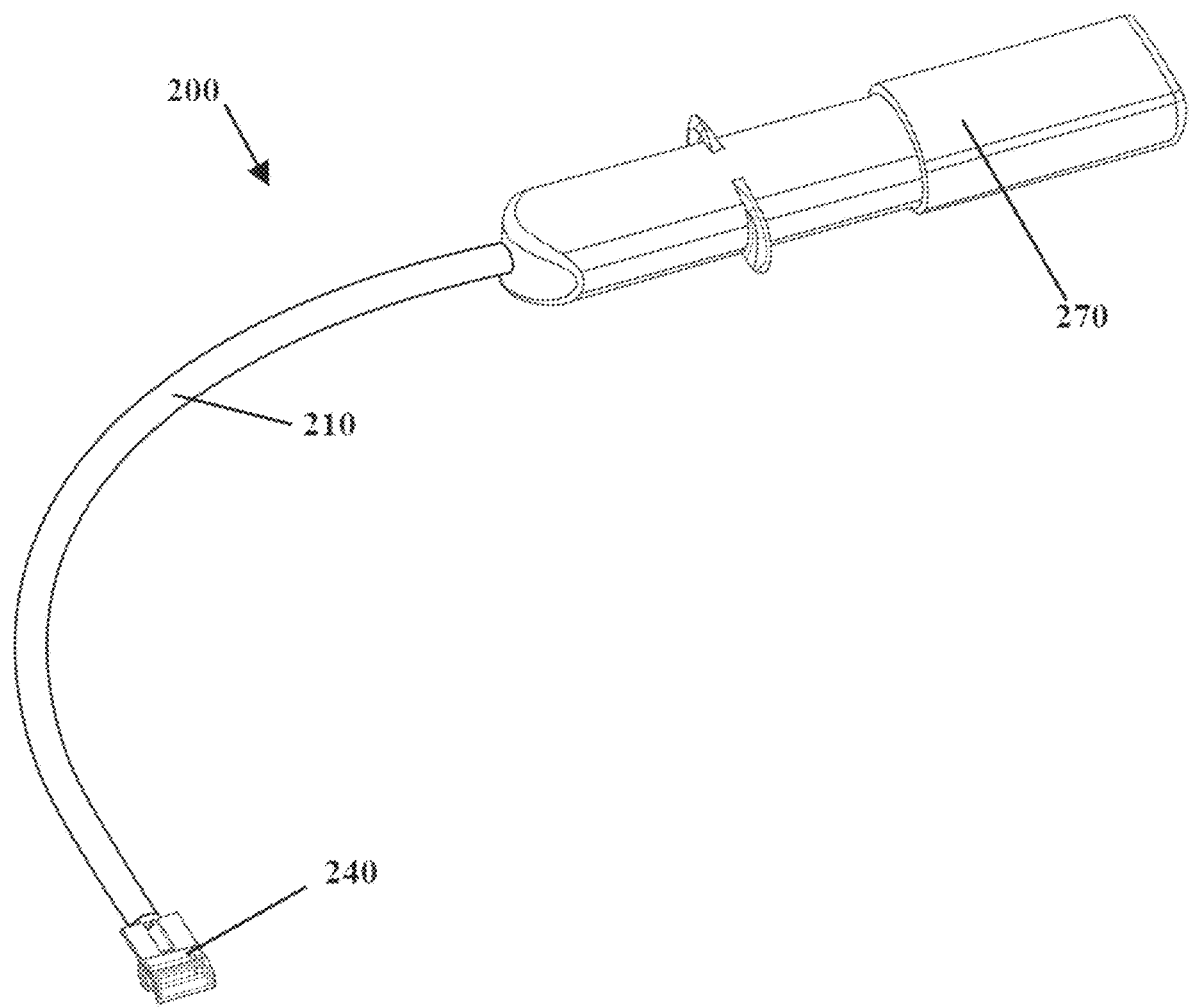
FIG. 6 illustrates an alternative embodiment of a device having a handle, a shaft, and an enclosure in accordance with the instant disclosure.
Figure 8:
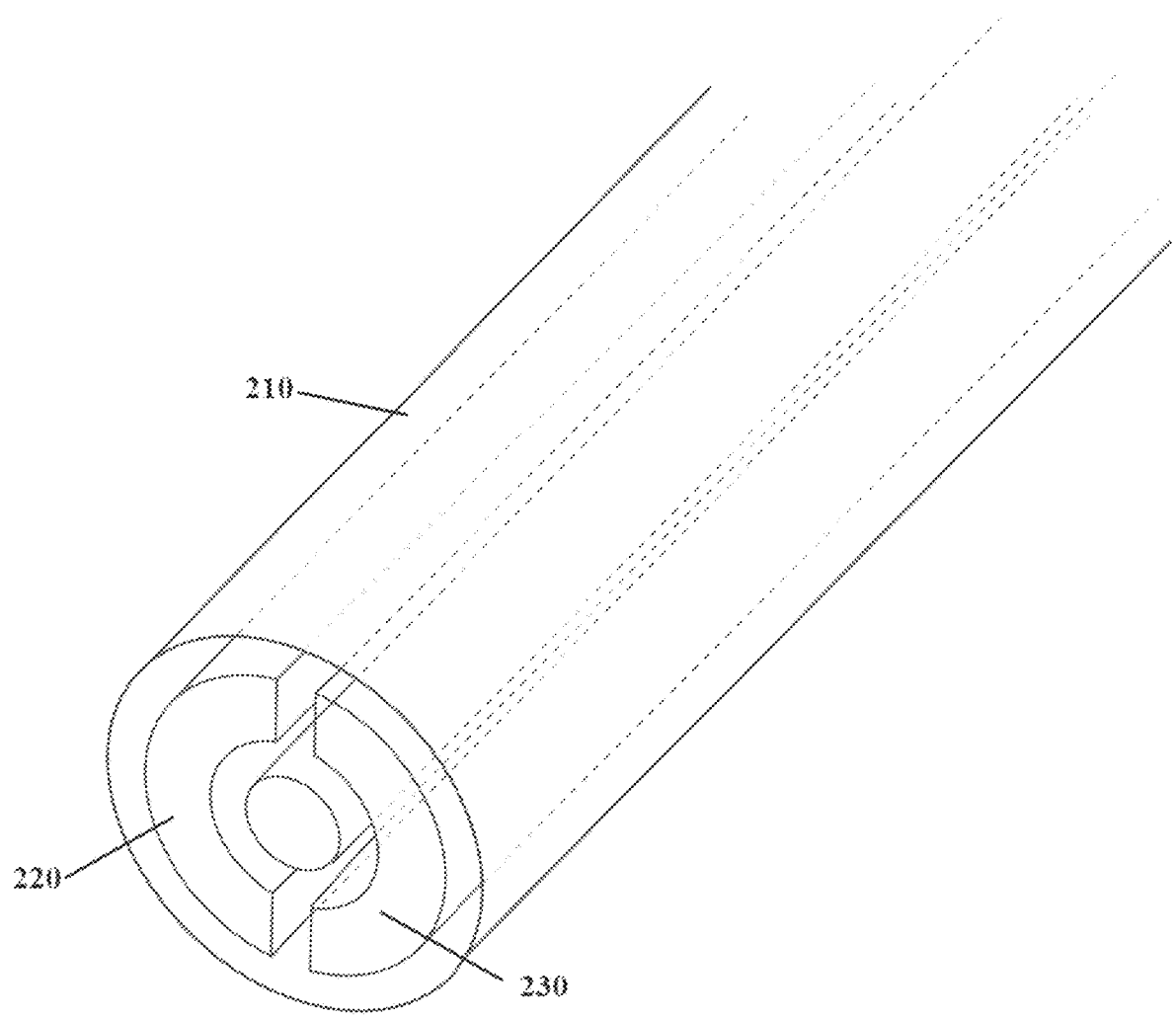
FIG. 8 illustrates a cross-sectional view of an embodiment of a shaft having a dispensing channel and an evacuating channel that are concentric, in accordance with the instant disclosure.
Figure 9A:
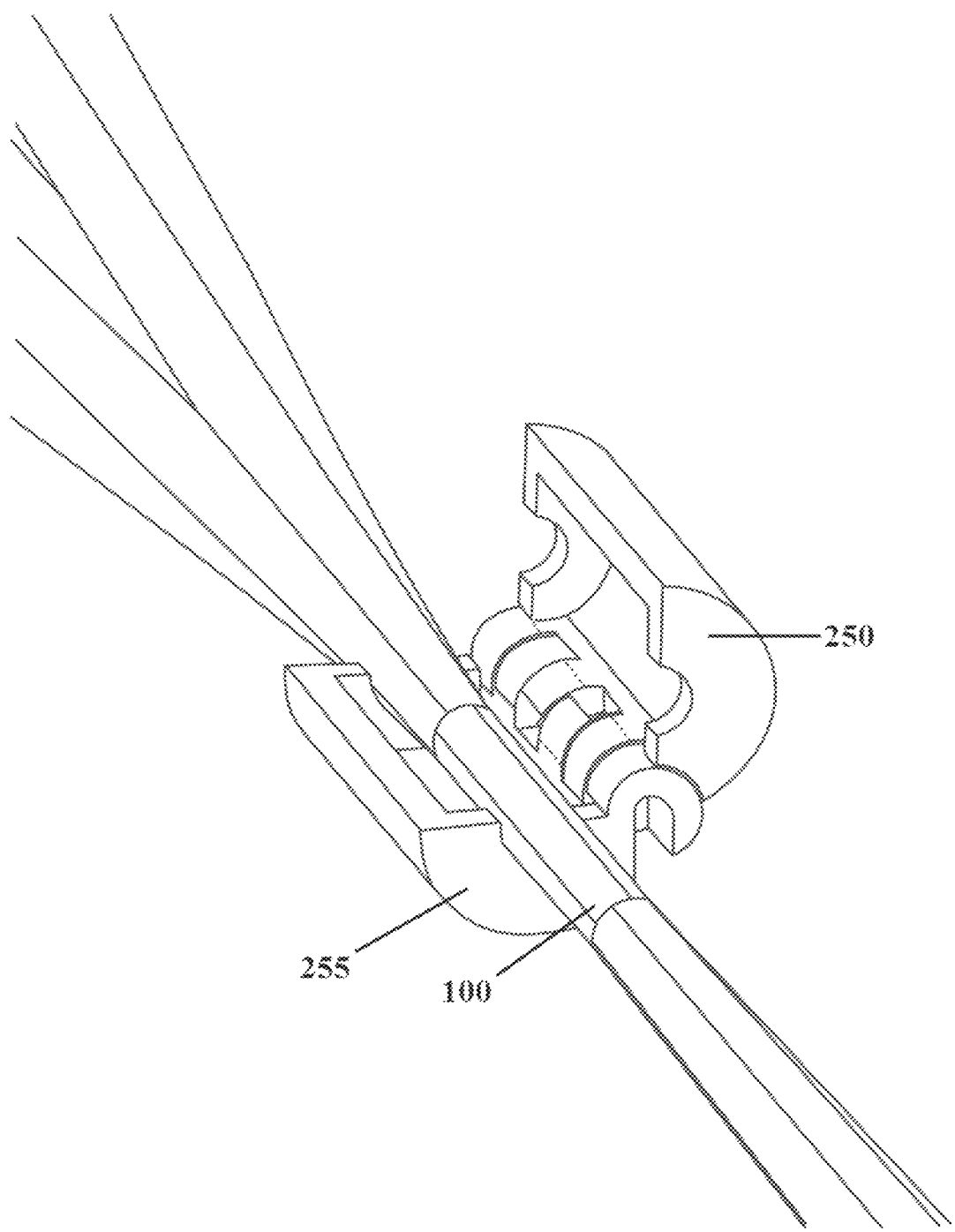
FIG. 9A illustrates an embodiment of an enclosure in an "open" position, wherein the first and second portions of the enclosure are connected by a hinge, in accordance with the instant disclosure.
Figure 9B:
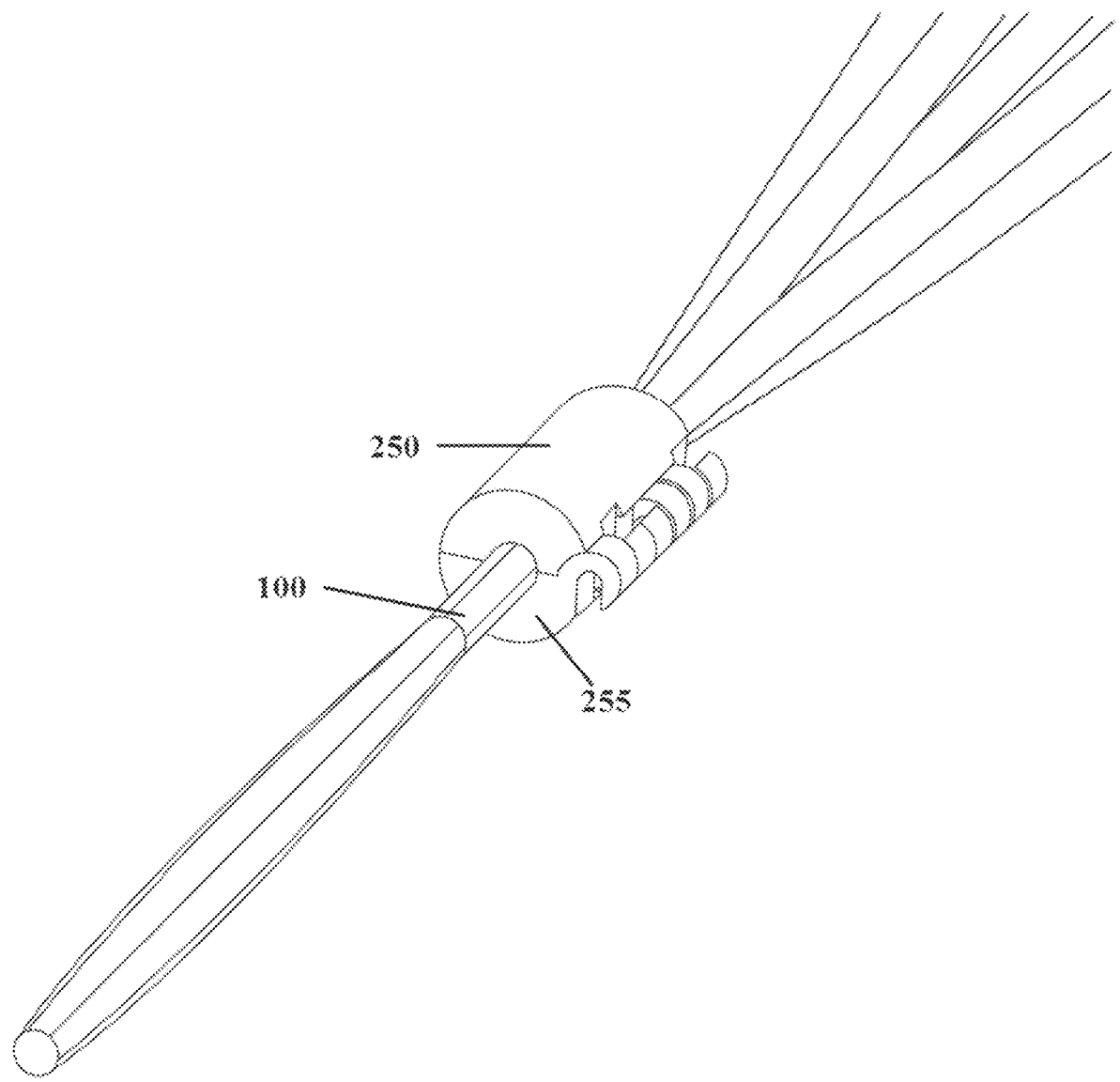
FIG. 9B illustrates the enclosure of FIG. 9A moved into a "closed" position to form a bore, in accordance with the instant disclosure.
Figure 10A:
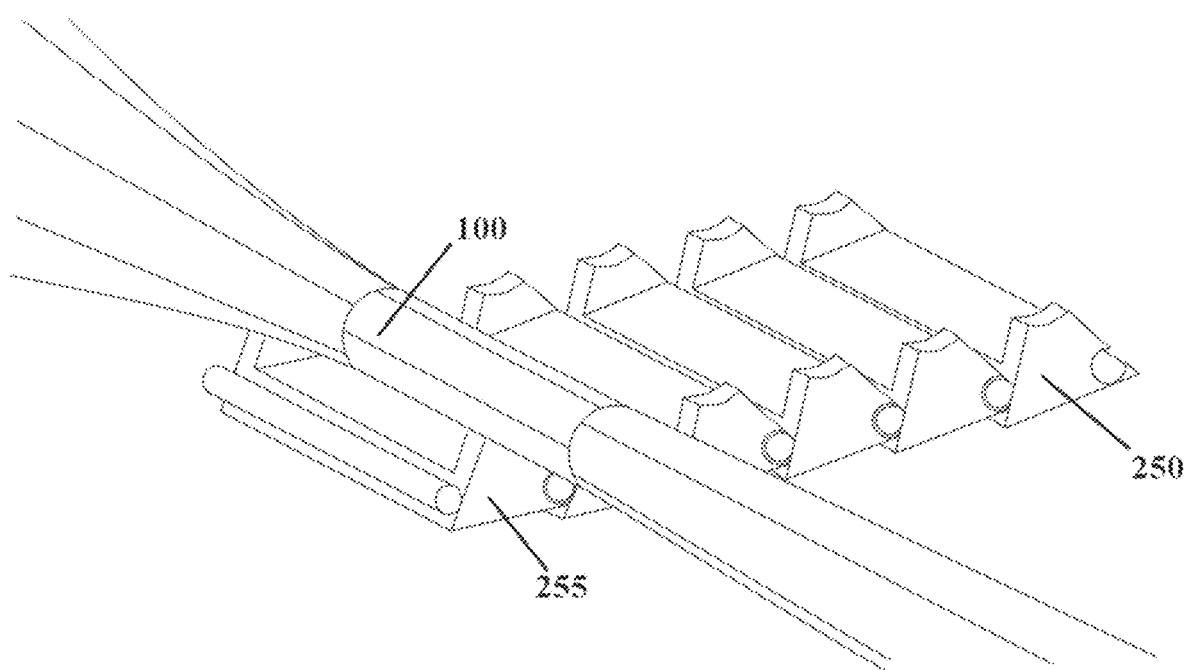
FIG. 10A illustrates an embodiment of an enclosure in an "open" position, wherein the enclosure has a hexagonal shape, in accordance with the instant disclosure.
Figure 10B:
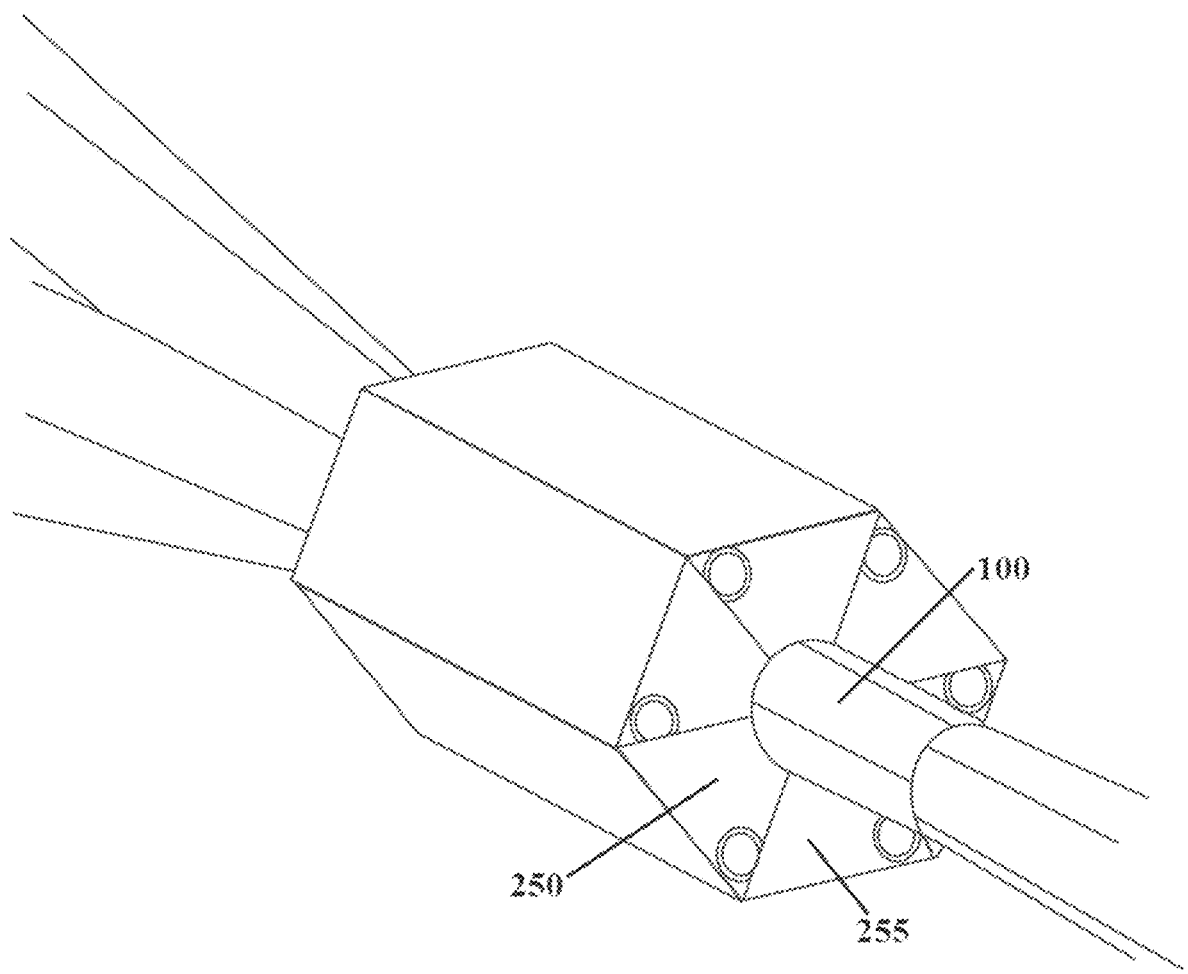
FIG. 10B illustrates the enclosure of FIG. 10A moved into a "closed" position to form a bore, in accordance with the instant disclosure.

The shaft of the device may further comprise a dispensing channel 220 and an evacuating channel 230. In some embodiments, one or both of the dispensing channel and the evacuating channel may be separate and independent of the shaft. In certain embodiments, each of the dispensing channel and the evacuating channel may independently comprise a biocompatible metal, a biocompatible plastic, a biocompatible glass, or any combination thereof. In some embodiments, each of the dispensing channel and the evacuating channel may comprise hollow tubes. In some embodiments, the dispensing channel 220 and the evacuating channel 230 may each be attached to an external portion of the shaft 210, as illustrated in FIG. 2. In other embodiments, the dispensing channel 220 and the evacuating channel 230 may be contained within the shaft 210, as illustrated in FIG. 6. In certain embodiments, the shaft 210, dispensing channel 220, and evacuating channel 230 may be concentric, as illustrated in FIG. 8. In an alternative embodiment, the dispensing channel may be attached to an external portion of the shaft, while the evacuating channel may be contained within the shaft. In still other embodiments, the dispensing channel may be contained within the shaft, while the evacuating channel is attached to an external portion of the shaft.

In some embodiments, the dispensing channel and the evacuating channel may each independently have a female luer lock port, or similar connecting port, at its proximal end. In certain embodiments, the dispensing channel and the evacuating channel may each independently have a reservoir at their proximal ends. In some embodiments, the reservoir may be detachable or removable, while in other embodiments the reservoir may be permanently or semi-permanently affixed to the dispensing channel or the evacuating channel. In certain embodiments, there may also be a valve between the reservoir and the proximal end of the either dispensing channel or the evacuating channel. Such a valve may be one-way or multi-way. In other embodiments, the connection between the reservoir and the dispensing channel or evacuating channel may be a manifold. The reservoir may be, for example, one or more syringes, one or more bags, or one or more canisters. In certain embodiments, the reservoir may further comprise one or more additional components such as, for example, an electronic pump, a pneumatic pump, a suction pump, a vacuum, and the like.

In some embodiments, the reservoir may be empty. In other embodiments, the reservoir may contain a solution. In certain embodiments, the solution may be any pharmaceutically acceptable solution. In some embodiments, the solution may comprise, for example, a membrane fusogen, poly(ethylene glycol), calcium, methylene blue, hypotonic saline, isotonic saline, nerve growth factor, glial cell-derived neurotropic factor, neurotrophin 3, brain-derived neurotrophic factor, insulin-like growth factor, platelet-derived growth factors, ciliary neurotrophic factors, fibroblast growth factor, erythropoietin, tacrolimus, cyclosporine, a nerve growth stimulation agent, air, a gas, a fluid, an antioxidant, a pharmaceutical, a biologic, or any combination thereof.

In other embodiments, the shaft, dispensing channel, and evacuating channel, or portions thereof may comprise one or more valves or similar flow structures. In certain embodiments, each of the dispensing channel and the evacuating channel may be independently opened or closed at either their proximal or distal ends using one or more such valves or similar flow structures. Furthermore, in some embodiments, the device may comprise a third channel having a mechanism configured to control the opening and closing of the enclosure.

In addition to the shaft 210, dispensing channel 220, and evacuating channel 230, the device further comprises an enclosure 240 attached to the distal end of the shaft 210, the enclosure 240 having a first portion 250 and a second portion 255, wherein the first portion 250 and the second portion 255 form a bore when the enclosure is closed. In certain embodiments, each first portion and second portion of the enclosure may independently comprise a biocompatible metal, a biocompatible plastic, a biocompatible glass, or any combination thereof. In certain embodiments, each component of the enclosure may independently comprise a non-neurotoxic polymer such as, for example, polycarbonate (PC), non-neurotoxic polymers, polypropylene (PP), polyethylene (PE), polyetheretherketone (PEEK), polysulfone (PS), polyethersulfone (PES), polytetrafluoroethylene (PTFE), polyoxymethylene (POM, Delrin), poly(N-2-hydroxypropyl methacrylamide), ethylene-co-vinyl acetate (EVA), polyvinyl acetate (PVAc), poly(methylmethacrylate) (PMMA), poly(dimethylsiloxane) (PDMS), acrylonitrile butadiene styrene (ABS), co-polymers thereof, or combinations thereof. In some embodiments, the enclosure may be substantially transparent, transparent, substantially translucent, translucent, or any combination thereof. In some embodiments, the enclosure may have an external shape such as, for example, a cylinder, a sphere, an ellipsoid, an ovoid, a hexagon, or any combination thereof. In some embodiments, the enclosure may further comprise other elements, such as, for example, a pressure relief mechanism or a cooling element. In certain embodiments, the pressure relief mechanism may be a check valve. In some embodiments, the cooling element may be configured to cool the repair site.

In some embodiments, the enclosure may have a first dimension of from about 5 mm to about 50 mm. The first dimension of the enclosure may be, for example, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, or any range between any two of these values, including endpoints.

In some embodiments, the bore that is formed when the first and second portions of the enclosure meet may itself have a diameter from about 1 mm to about 30 mm. The diameter of the bore may be, for example, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, or any range between any two of these values, including endpoints.

Figure 3:
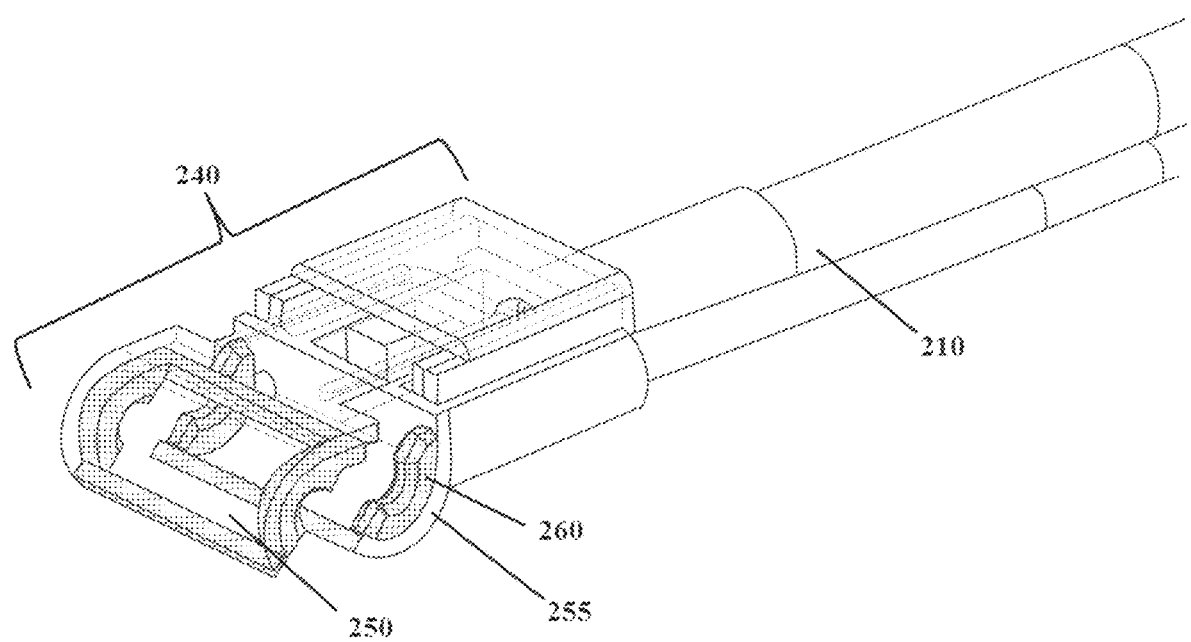
FIG. 3 illustrates an embodiment of a distal end of a shaft with an enclosure, in accordance with the present disclosure.
Figure 4:
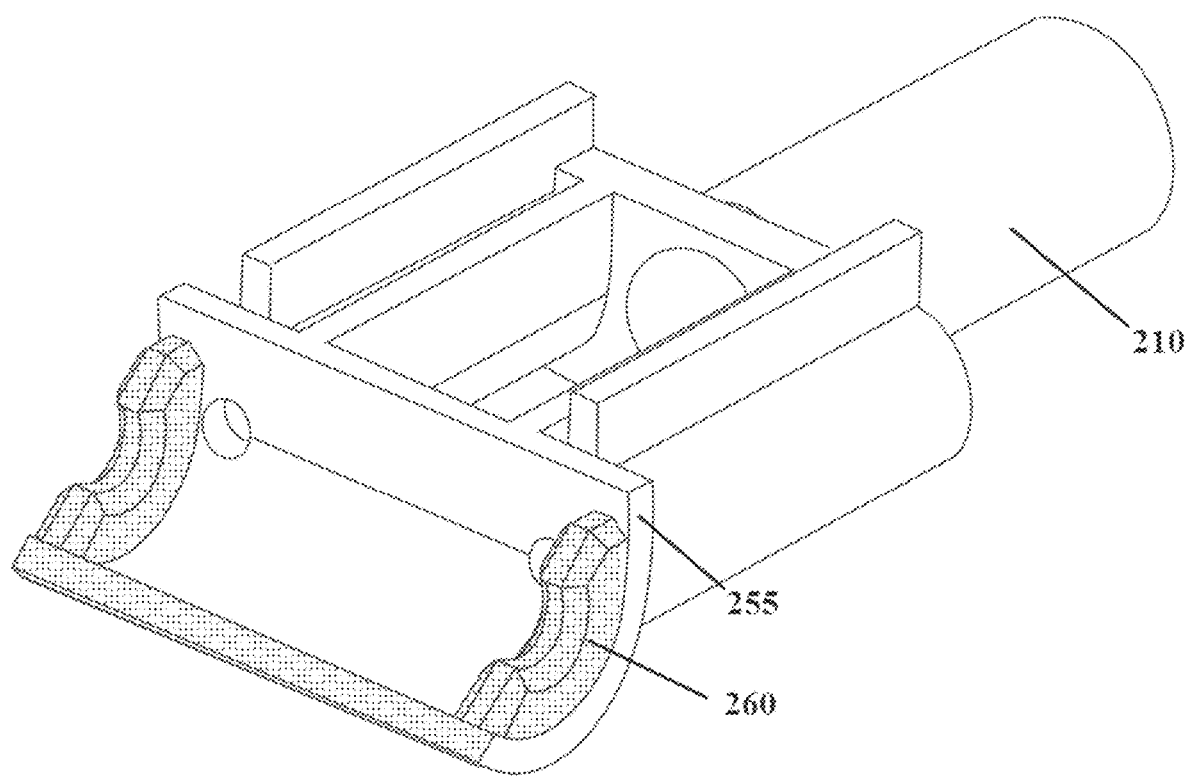
FIG. 4 illustrates an embodiment of a second portion of an enclosure in accordance with the present disclosure.
Figure 5:
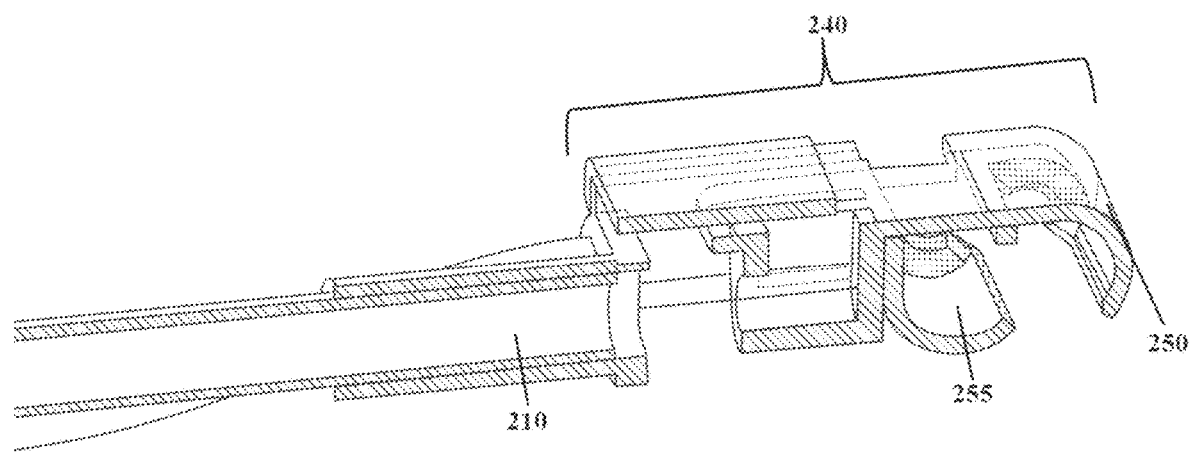
FIG. 5 illustrates a cross-sectional view of an embodiment of a distal end of a shaft with an enclosure, in accordance with the present disclosure.

In some embodiments, each of the first portion 250 and the second portion 255 may independently further comprise a material 260 configured to seal the enclosure around a lumen 100, as illustrated in FIG. 3 and FIG. 4. In some embodiments, the lumen 100 may comprise a nerve repair site 110, as illustrated in FIG. 1. In certain embodiments, the nerve repair site 110 may comprise one or more microsutures, while in other embodiments, the nerve repair site 110 may not comprise any microsutures. In some embodiments, the material 260 may be flexible. In one embodiment, the material 260 may be at the ends of the first 250 and second 255 portions, while in another embodiment, the material 260 may be along an section of the first 250 and second 255 portions that contacts the lumen 100 or a portion thereof. In certain embodiments, the material may be a soft silicone. In still other embodiments, the material may comprise a feathered edge. In some embodiments, the seal around the lumen may be water-tight seal. In other embodiments, the seal may be substantially water-tight. In still other embodiments, the seal may be air-tight or substantially air-tight.

In some embodiments, the first portion 250 of the enclosure 240 and the second portion 255 of the enclosure 240 may be connected by one or more hinges, as illustrated in FIG. 9A, FIG. 9B, FIG. 10A, and FIG. 10B. (The shaft and other components have been omitted for clarity in these figures.) In other embodiments, the first and second portions of the enclosure may be connected by one or more flexure bearings. In still other embodiments, the first and second portions of the enclosure may be connected by one or more clips. In certain embodiments, one or more clips may be used to secure the first and second portions of the enclosure in the "closed" position. Other arrangements may be employed to facilitate "opening" and "closing" the enclosure.

In certain embodiments, the dispensing channel of the device may be configured to deliver a solution, as described above, to the bore of the enclosure. Similarly, in some embodiments, the evacuating channel may be configured to remove the solution from the bore of the enclosure. In certain embodiments, the surface of the enclosure that forms the bore when closed may further comprise one or more ports. In some embodiments, the ports may be communicably connected to the dispensing channel, the evacuating channel, or both. The ports may serve as inlets, outlets, or a combination thereof. In certain embodiments, the one or more ports may be configured to deliver a solution, as described above, from the dispensing channel to the lumen around which the enclosure is closed. In such embodiments, the ports may also be configured to remove the solution, as described above, from the lumen to the evacuating channel. In certain embodiments, the ports may independently comprise a biocompatible metal, a biocompatible plastic, a biocompatible glass, or any combination thereof. In other embodiments, the ports may independently comprise sintered glass, sintered metal, sintered plastic, or any combination thereof. In some embodiments, the ports may independently comprise a non-neurotoxic polymer, as described above. In certain embodiments, the ports may be used to deliver a solution as a fine mist. In certain embodiments, at least one of the first and second portions of the enclosure may be hollow and may contain holes that serve as ports for dispensing and evacuation. In one embodiment, only one of the first and second portions of the enclosure may be hollow and may contain holes that serve as ports for dispensing and evacuation. In other embodiments, the ports may be used to deliver a solution as a spray or droplets. In still other embodiments, the enclosure may contain multiple holes that function substantially similarly to the ports described herein. In some embodiments, the multiple holes may comprise micro-holes. In some embodiments, such delivery and removal of a solution may help improve nerve repairs by delivering the solution uniformly to the nerve repair site.

Figure 7A:
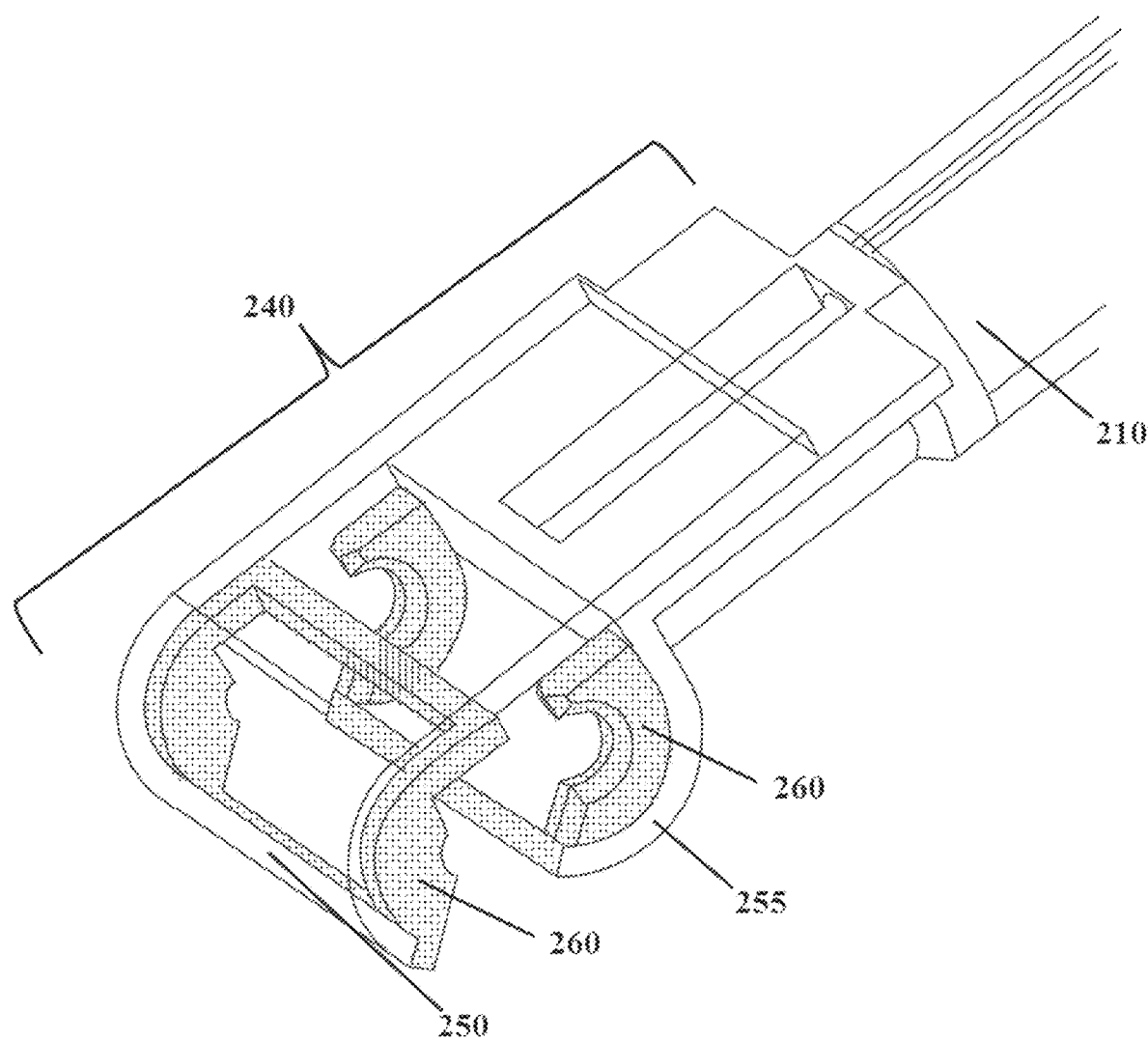
FIG. 7A illustrates an embodiment of an enclosure in an "open" position, in accordance with the instant disclosure.
Figure 7B:
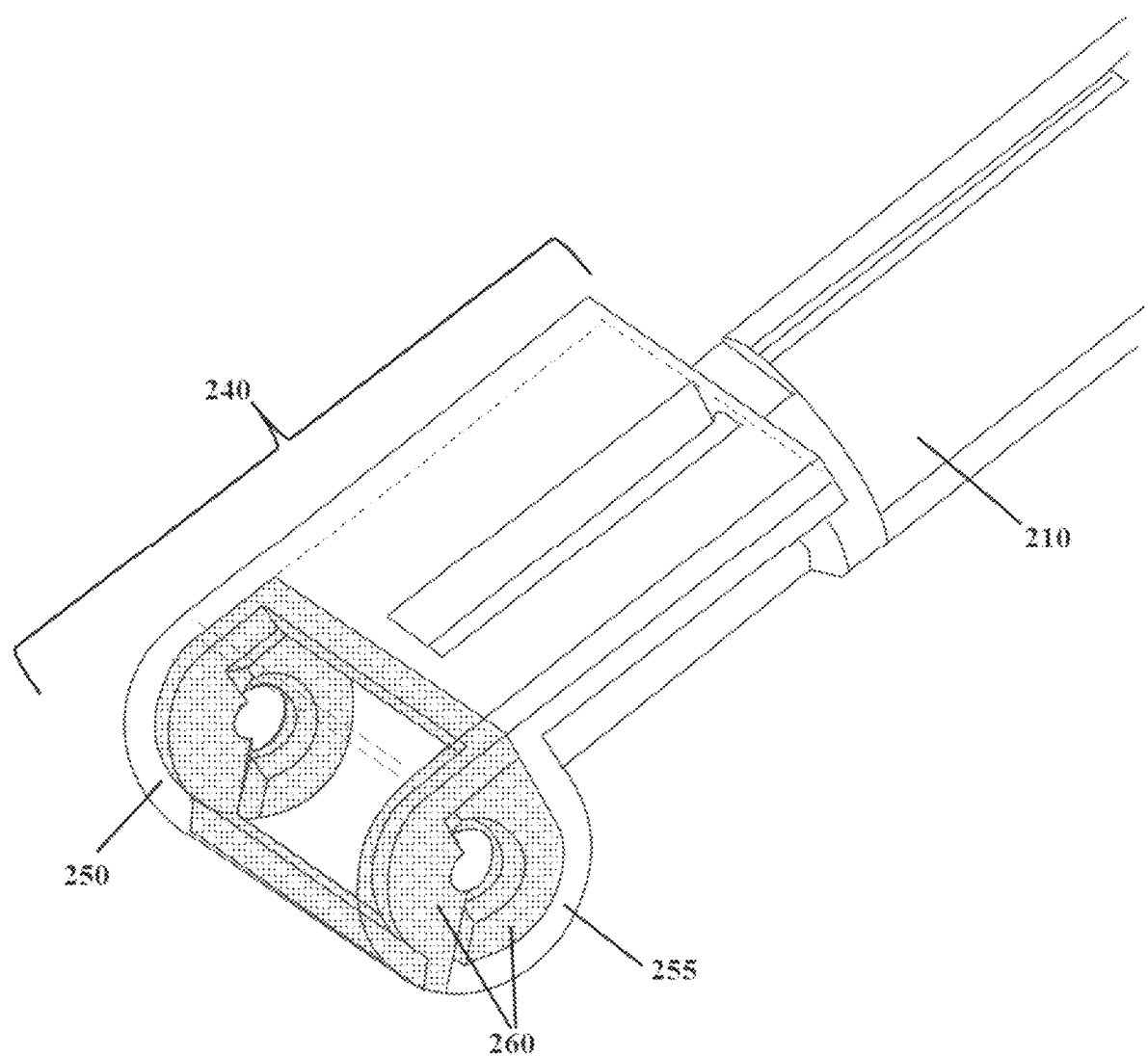
FIG. 7B illustrates the enclosure of FIG. 7A moved into a "closed" position to form a bore, in accordance with the instant disclosure.

The device 200 may still further comprise a handle 270 attached to the proximal end of the shaft 210 and configured to open and close the enclosure 240. In some embodiments, the handle may be configured to mechanically open and close the enclosure, while in other embodiments, the handle may be configured to open and close the enclosure using a spring or spring-loaded device. In still other embodiments, the handle may be configured to open and close the enclosure by sliding at least one of the first portion and the second portion. The handle 270 may be configured to, for example, slide the first portion 250 of the enclosure 240 to meet the second portion 255 of the enclosure 240, as illustrated in FIG. 7A and FIG. 7B. In certain embodiments, the handle may comprise a sliding mechanism, a hinge mechanism, a triggering mechanism, a spring-loaded mechanism, or any combination thereof, for opening and closing the enclosure. In some embodiments, a second, removable handle may be attached directly to the enclosure to allow for initial engagement of the enclosure with the nerve repair site.

Figure 11A:
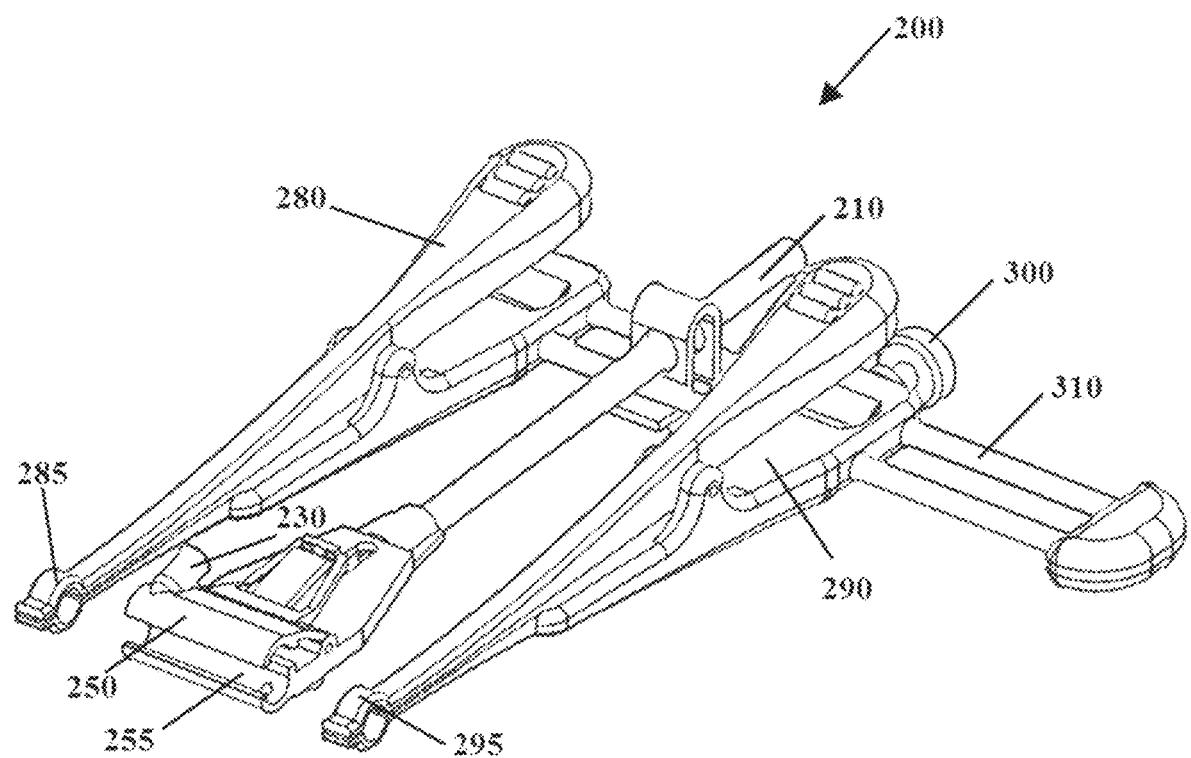
FIG. 11A illustrates a prospective view of an embodiment of a device having a shaft, an enclosure, a bar, a first clamp, a second clamp, and a locking mechanism in accordance with the instant disclosure.
Figure 11B:
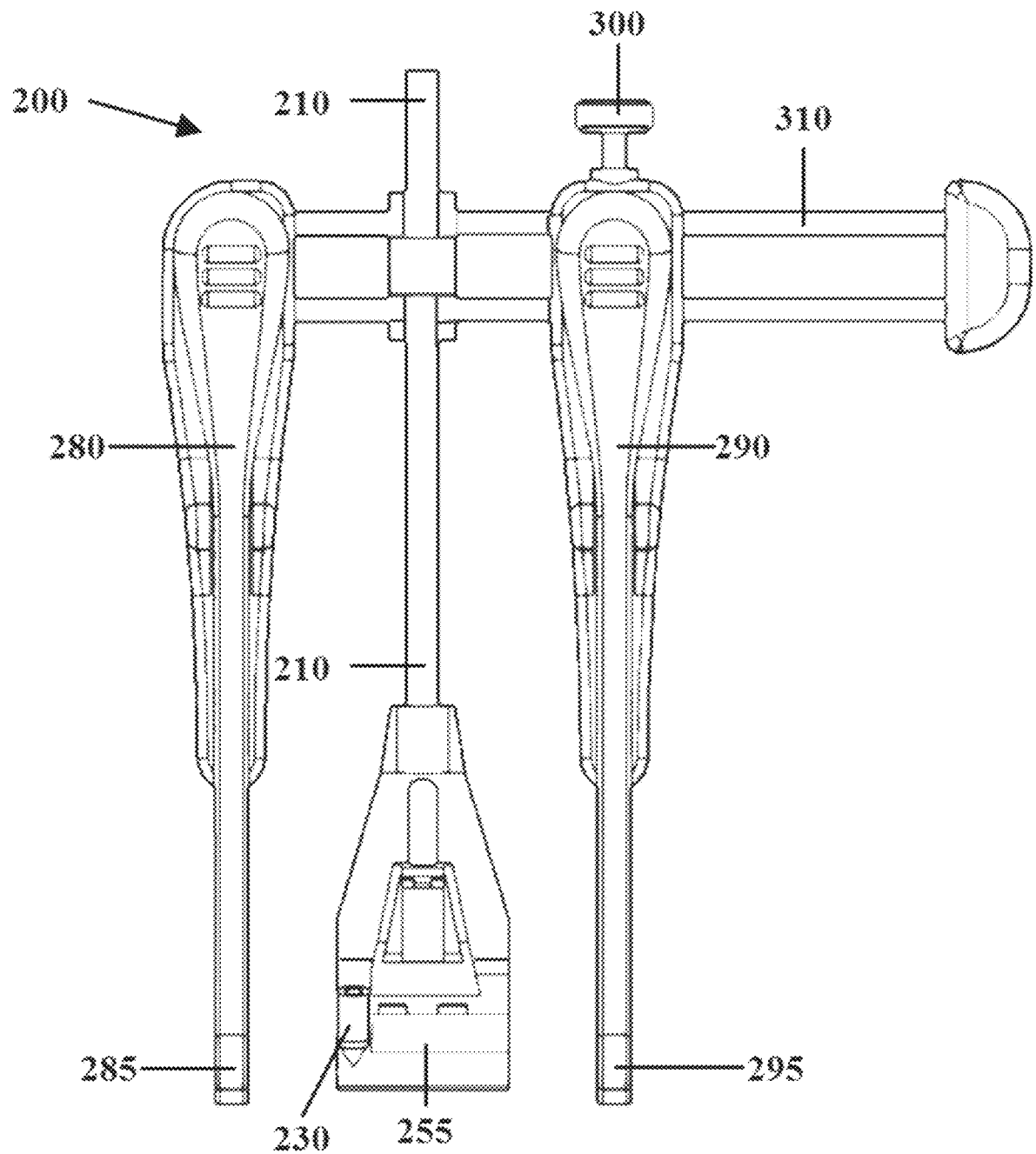
FIG. 11B illustrates a top view of an embodiment of a device having a shaft, an enclosure, a bar, a first clamp, a second clamp, and a locking mechanism in accordance with the instant disclosure.

In some embodiments, such as the embodiment illustrated in FIG. 11A and FIG. 11B, the device may comprise a bar 310, with the shaft 210 slideably engaged with the bar 310. In some embodiments, the bar may comprise a U-hook. The shaft 210 may be oriented orthogonally with respect to the bar 310. The device may further comprise the enclosure 240 attached to the distal end of the shaft 210, the enclosure 240 comprising the dispensing channel 220, the evacuating channel 230, the first portion 250, and the second portion 255, wherein the first portion 250 and the second portion 255 form a bore when the enclosure 240 is closed, as described above. The device may further comprise a first clamp 280 engaged with the bar 310, and a second clamp 290 engaged with the bar 310. The shaft 210 may be positioned between the first clamp 280 and the second clamp 290. The device may still further comprise a locking mechanism 300 configured to fix, or lock, the position of the first clamp 280, the second clamp 290, or a combination thereof, along the bar 310. In certain embodiments, the first clamp may be fixedly engaged with the bar, the second clamp may be slideably engaged with the bar, and the locking mechanism may be configured to fix the position of the second clamp along the bar. The locking mechanism may comprise, for example, a wheel, a screw mechanism, and the like.

In certain embodiments, the first clamp 280 may have a distal end 285 configured to grip at least a portion of a lumen 100. In some embodiments, the second clamp 290 may have a distal end 295 configured to grip at least a portion of the lumen 100. In certain embodiments, each of the distal end 285 of the first clamp 280 and the distal end 295 of the second clamp 290 are configured to grip the portion of the lumen while preventing compression of the lumen. Preventing compression is particularly important when the lumen comprises a nerve, because compressing the nerve will damage it.

Method of Use

A method for delivering a solution to a nerve repair site may comprise obtaining a device as described herein, closing the enclosure around the nerve repair site such that the nerve repair site occupies the bore of the enclosure, delivering one or more solutions through the dispensing channel to the nerve repair site, removing the one or more solutions through the evacuating channel from the nerve repair site, and opening the enclosure to remove it from the nerve repair site. In certain embodiments, the method may further comprise pressurizing the enclosure while it is closed around the nerve repair site. The pressurization may occur by, for example, delivering a fluid or gas to the enclosure via the dispensing channel. In some embodiments, pressurizing the enclosure may comprise delivering the one or more solutions to the enclosure via the dispensing channel while the evacuating channel is closed. In certain embodiments, delivering the one or more solutions to the enclosure via the dispensing channel may further comprise using an external pressure source. The external pressure source may or may not be removably attached to the dispensing channel. Such pressurization may allow a solution to penetrate a nerve bundle without injuring the nerve.

In some embodiments, closing the enclosure around the nerve repair site may comprise sliding the first portion of the enclosure to meet the second portion of the enclosure, as illustrated in FIG. 7A and FIG. 7B. In other embodiments, closing the enclosure around the nerve repair site may comprise activating a spring mechanism to bring the first portion of the enclosure and the second portion of the enclosure together. In still other embodiments, closing the enclosure around the nerve repair site may further comprise engaging a clip to lock the first portion of the enclosure and the second portion of the enclosure around the nerve repair site.

Figure 12A:
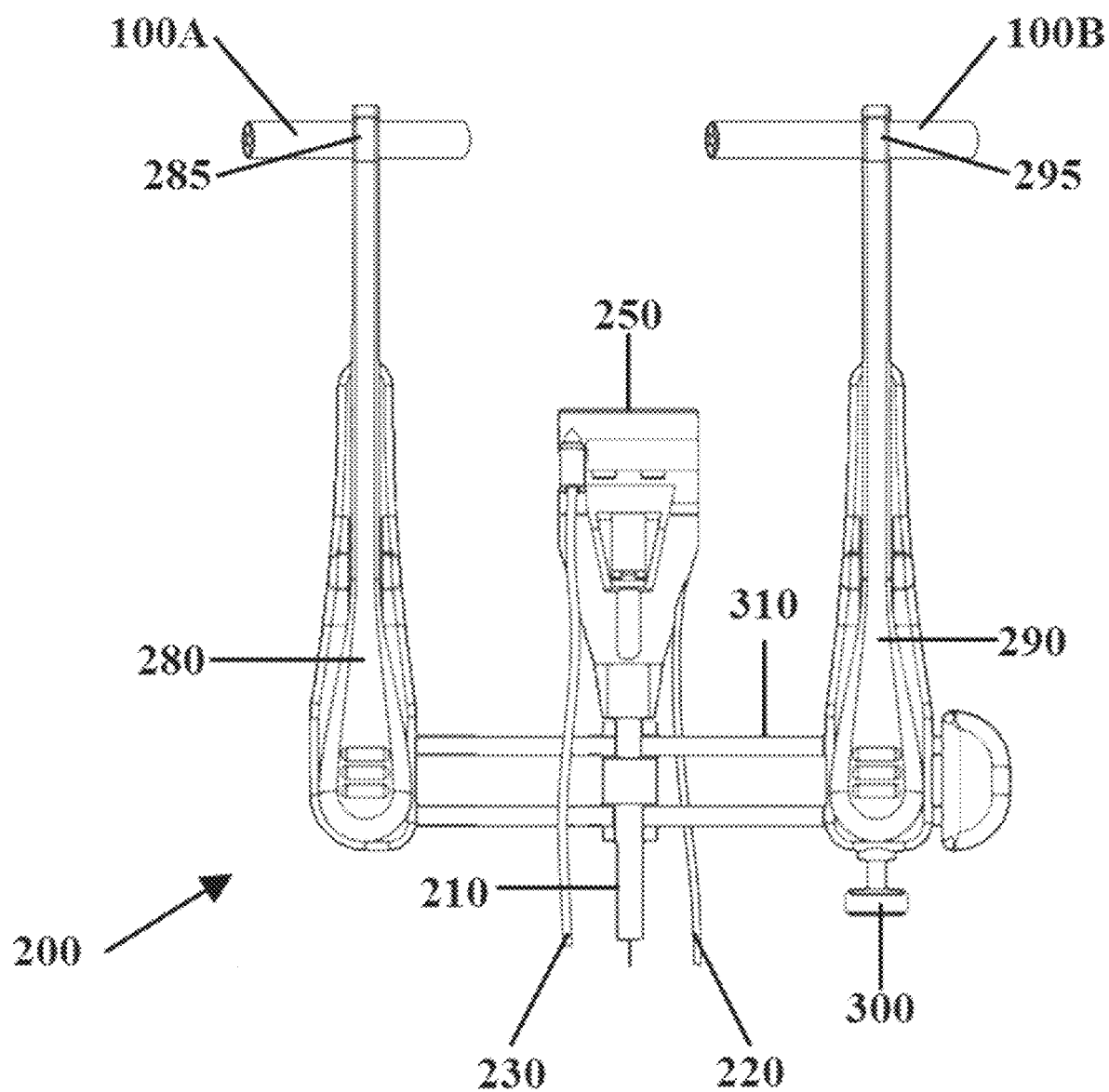
FIG. 12A illustrates an embodiment of the step of engaging each of a distal end of a first clamp and a distal end of a second clamp with a first and second portion of a severed nerve, respectively, as part of a method of repairing a severed nerve in accordance with the instant disclosure.
Figure 12B:
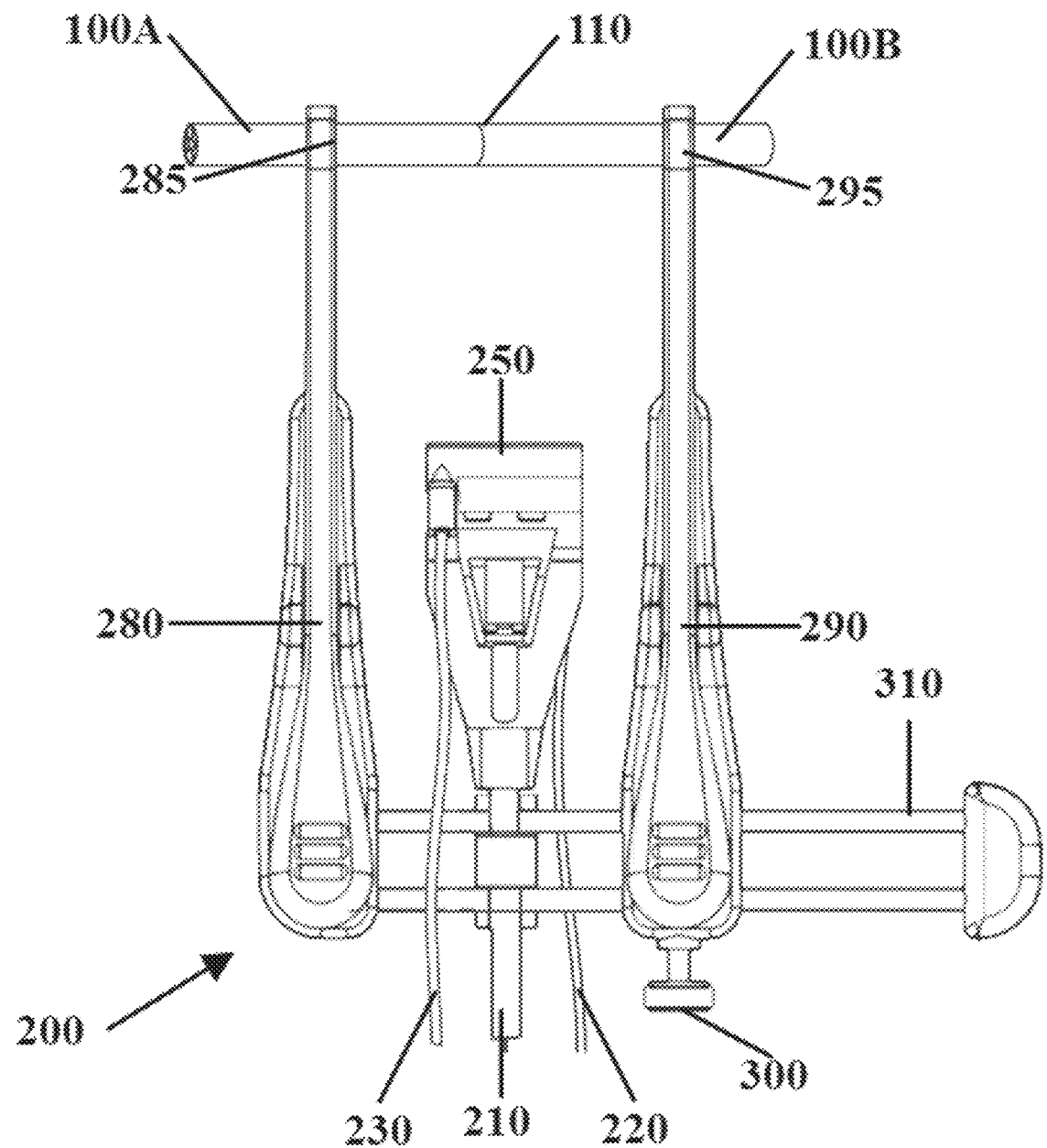
FIG. 12B illustrates an embodiment the step of sliding a first clamp, a second clamp, or a combination thereof along a bar to position a first portion of a severed nerve substantially adjacent to a second portion of the severed nerve to form a nerve repair site, as part of a method of repairing a severed nerve in accordance with the instant disclosure.
Figure 12C:
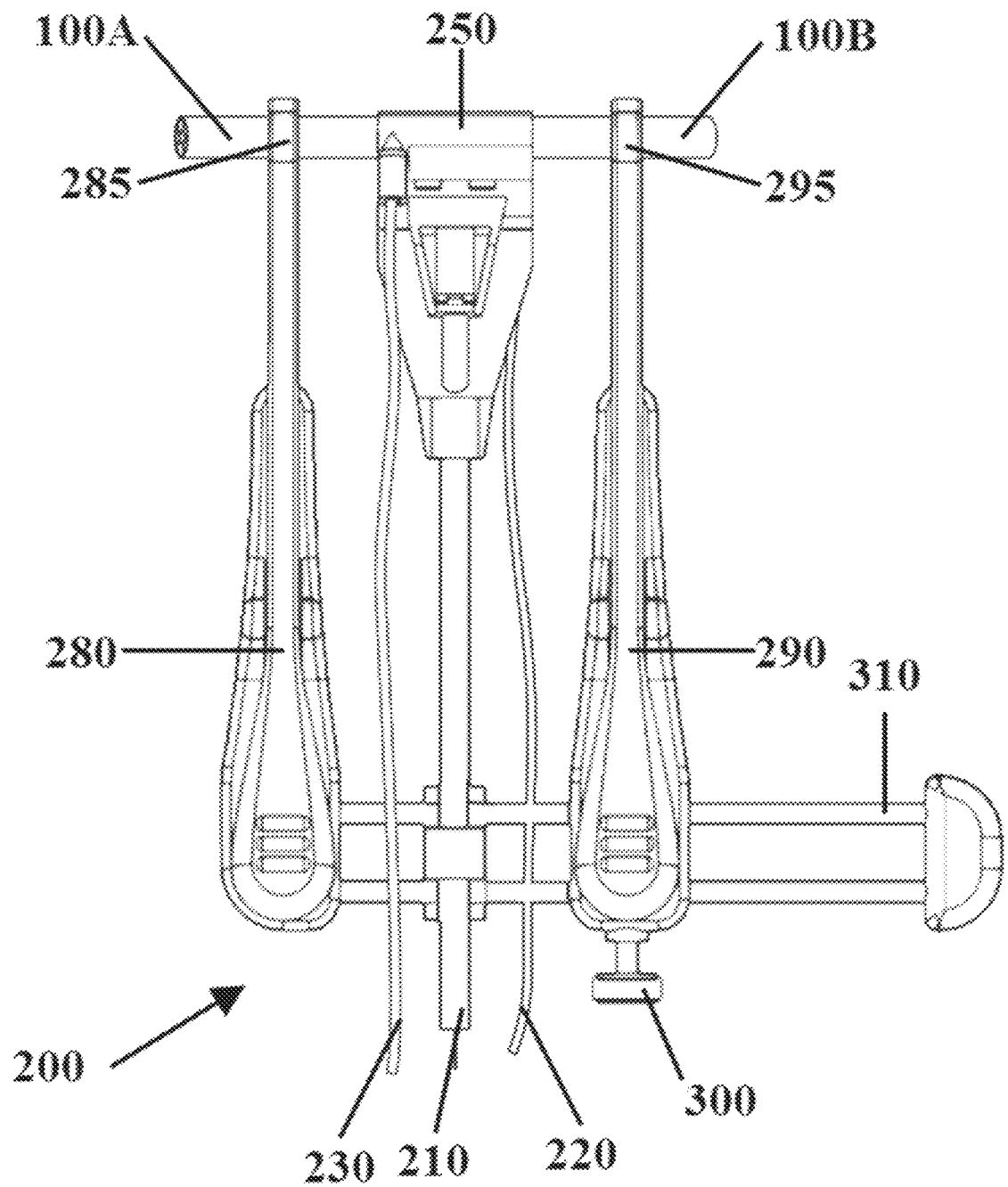
FIG. 12C illustrates an embodiment of closing an enclosure around a nerve repair site, such that the nerve repair site occupies a bore of the enclosure, as part of a method of repairing a severed nerve in accordance with the instant disclosure.
Figure 12D:
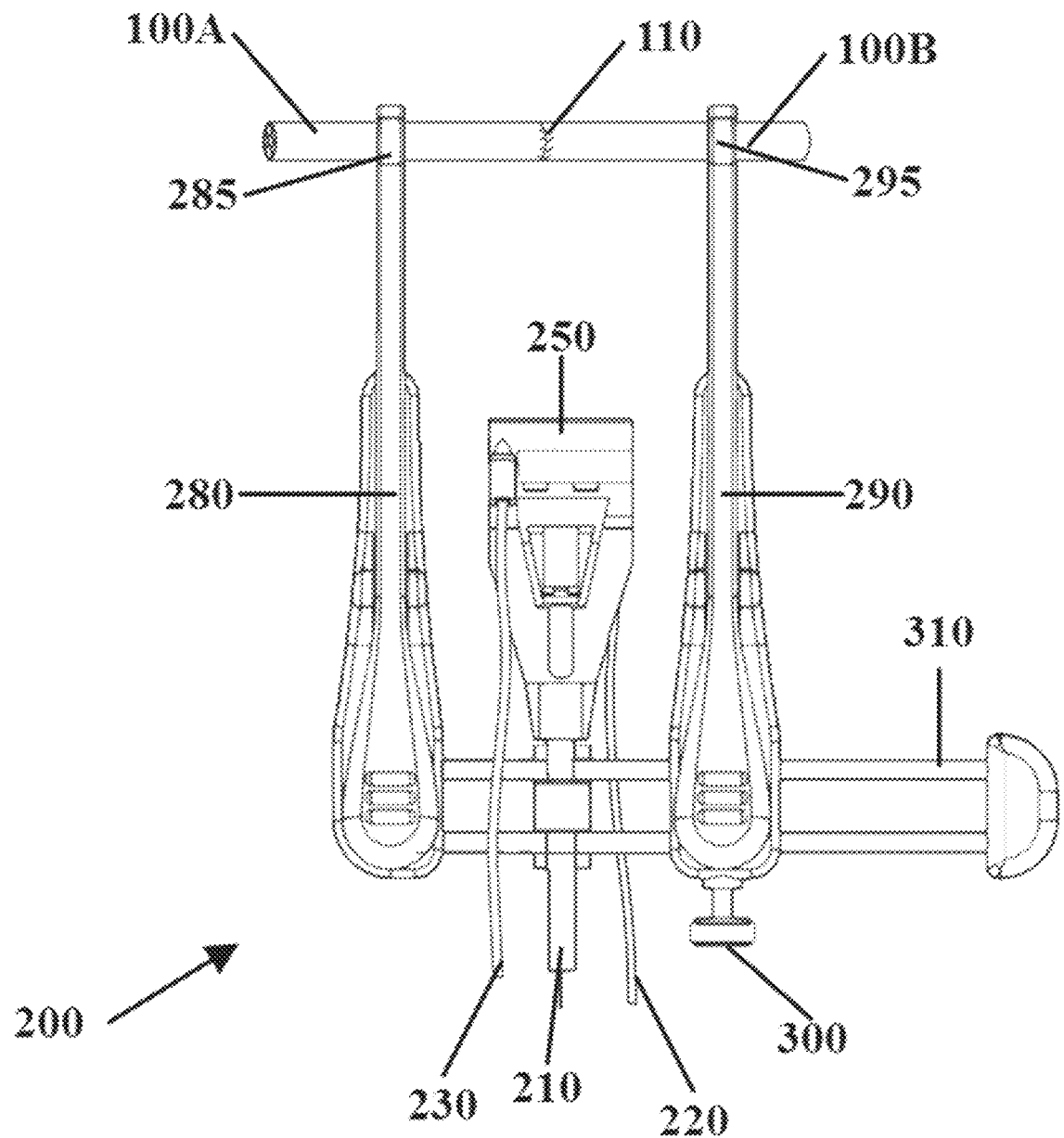
FIG. 12D illustrates an embodiment of opening an enclosure to remove it from a nerve repair site, followed by applying one or more microsutures to the nerve repair site, as part of a method of repairing a severed nerve in accordance with the instant disclosure.
Figure 12E:
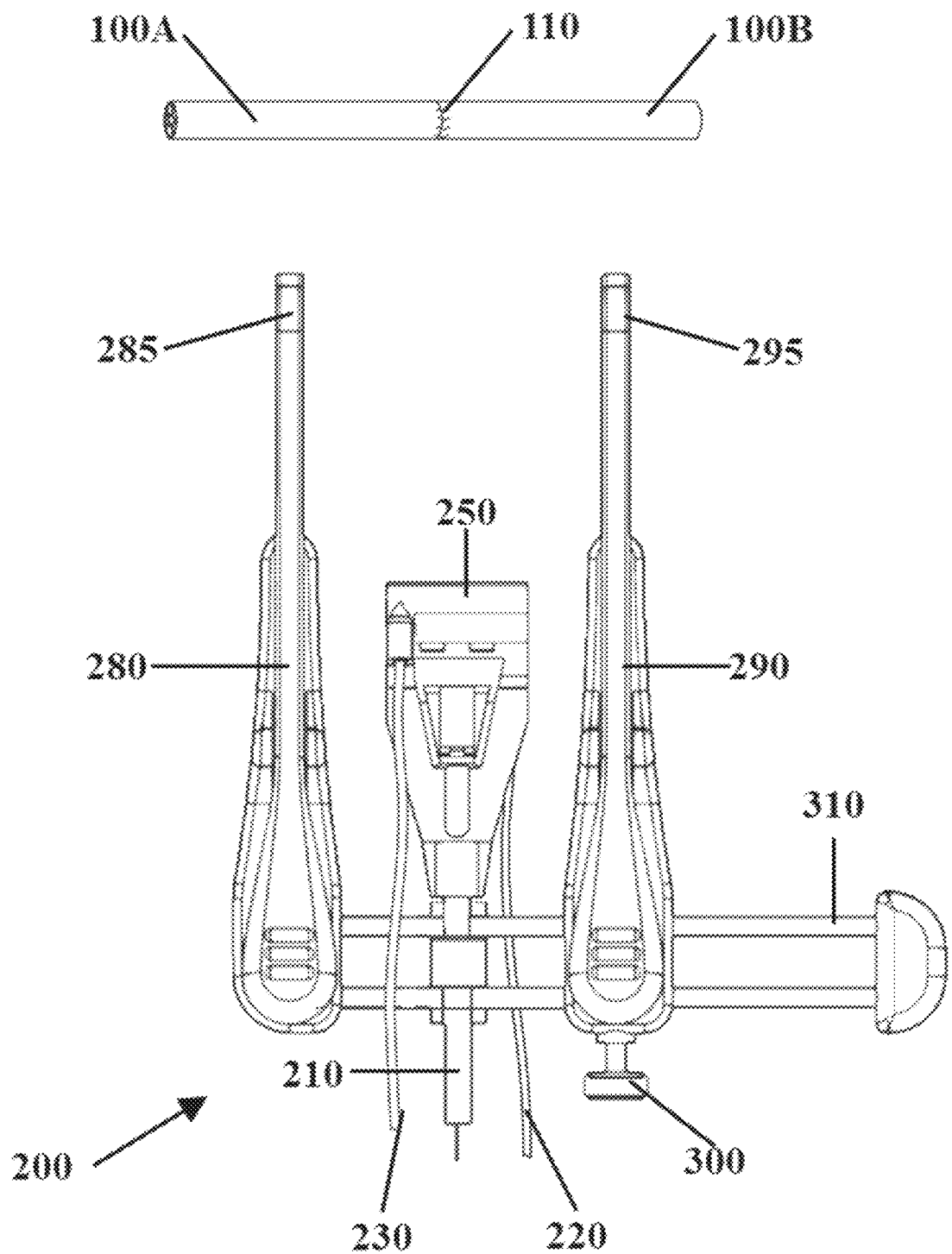
FIG. 12E illustrates an embodiment releasing a first clamp from a first portion of a severed nerve, and releasing a second clamp from a second portion of the severed nerve, as part of a method of repairing a severed nerve in accordance with the instant disclosure.
Figure 13:
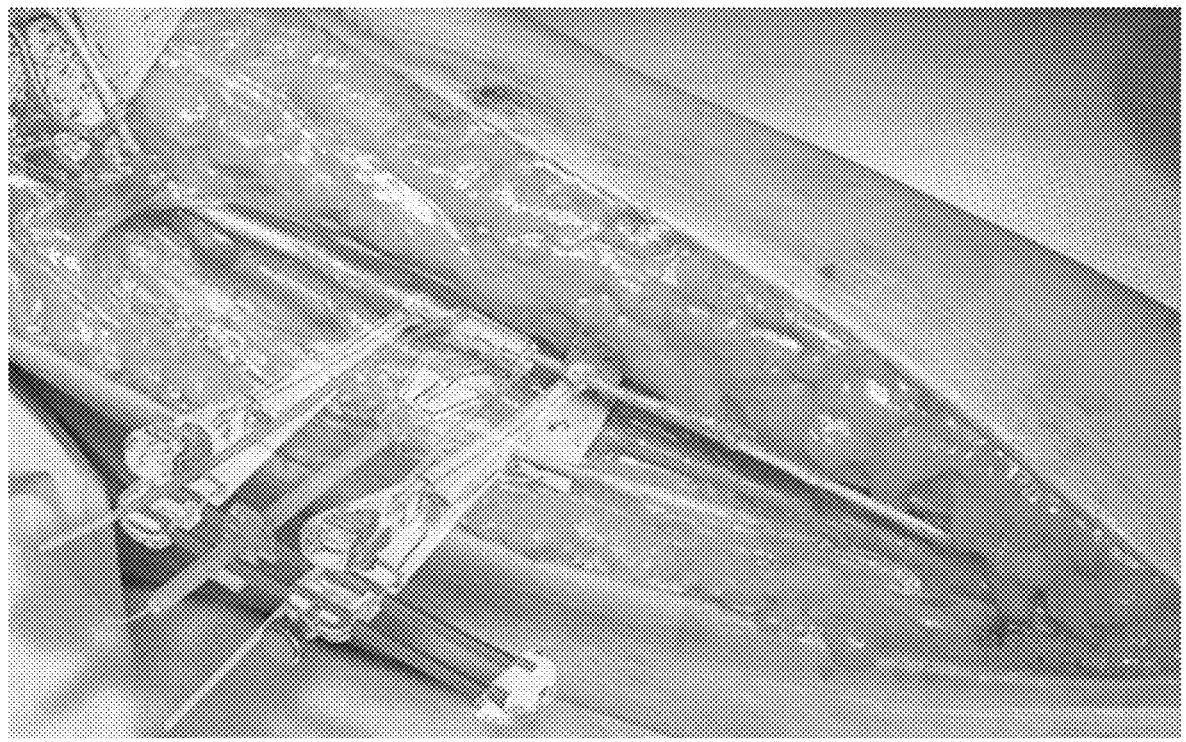
FIG. 13 illustrates an embodiment of a device engaged with model of a human peripheral nerve in accordance with the instant disclosure.

In other embodiments, a method for repairing a severed nerve may comprise obtaining a device as described herein, engaging the distal end of the first clamp with a first portion 100A of the severed nerve, engaging the distal end of the second clamp with a second portion 100B of the severed nerve, and sliding first clamp, the second clamp, or a combination thereof, along the bar to position the first portion of the severed nerve substantially adjacent to the second portion of the severed nerve to form a repair site (FIG. 12A and FIG. 12B). The method may further comprise engaging the locking mechanism to fix the position of the first clamp, the second clamp, or a combination thereof, along the bar, closing the enclosure around the nerve repair site, such that the nerve repair site occupies the bore of the enclosure, delivering a solution through the dispensing channel to the nerve repair site, and removing the solution through the evacuating channel from the nerve repair site (FIG. 12C). The method may still further comprise opening the enclosure to remove it from the nerve repair site, releasing the first clamp from the first portion of the severed nerve, and releasing the second clamp from the second portion of the severed nerve (FIG. 12D and FIG. 12E). In some embodiments, the method may further comprise applying one or more microsutures to the nerve repair site (FIG. 12D). Applying the microsutures may be done before or after delivering the solution to the nerve repair site and removing the solution from the nerve repair site. Embodiments of the steps of such a method are illustrated in FIG. 12A, FIG. 12B, FIG. 12C, FIG. 12D, and FIG. 12E, as noted above. In addition, an embodiment of a device engaged with a model of a human peripheral nerve according to such a method is illustrated in FIG. 13, which is a computer-generated illustration. Employing the devices and methods described herein, a method of nerve repair may comprise administering calcium-free hypotonic saline to the axon ends, microsuturing the ends together to form a nerve repair site as illustrated in FIG. 1, and closing the enclosure around the nerve repair site as described herein. Once the enclosure is secured around the nerve repair site, one or more solutions or mixtures containing various nerve regeneration promoters or immunosuppressants may be administered to the nerve repair site. The one or more solutions or mixtures may include, for example, membrane fusogen, poly(ethylene glycol), calcium, methylene blue, hypotonic saline, isotonic saline, nerve growth factor, glial cell-derived neurotropic factor, neurotrophin 3, brain-derived neurotrophic factor, insulin-like growth factor, platelet-derived growth factors, ciliary neurotrophic factors, fibroblast growth factor, erythropoietin, tacrolimus, cyclosporine, a nerve growth stimulation agent, tacrolimus, cyclosporine, air, a gas, a fluid, an antioxidant, a pharmaceutical, a biologic, or combinations thereof. In one embodiment, the following solutions may be administered to the site via the dispensing channel: (1) a methylene blue solution, (2) a PEG solution, and (3) an isotonic saline bath containing calcium. After each solution is administered to the site, it may then be removed from the site by, for example, using the evacuating channel to apply a vacuum. The nerve repair device may be applied to and removed from the nerve repair site between the administration of each solution, or the entire protocol may be performed while the device is closed around the nerve repair site. Once each of these solutions has been administered to the nerve repair site, the device may then be opened and removed from the site, leaving a repaired nerve. It should be noted that administering the solution(s) to the nerve repair site may occur after the axon ends have been microsutured, as described above, or may occur even before the axon ends are microsutured. Without wishing to be bound by theory, administering the solution(s) to the nerve repair site before the axon ends are microsutured may facilitate the delivery of the solution(s) to the internal structures of the axon ends, and the penetration of the solution(s) into the nerve tissues, which may improve nerve healing. Said another way, the number of microsutures required to give the nerve repair site the appropriate mechanical strength may hinder the penetration of the solution(s) into the nerve bundle, where they need to reach to fuse the axon ends.

Kit

In certain embodiments, a kit comprises a device as described herein, and one or more syringes. The kit may comprise a single syringe, or more than one syringe. In some embodiments, the syringe(s) comprise a plastic material. The syringes may be sterile, and may include a luer lock attachment. In some embodiments, each syringe may contain a solution or mixture as described herein. In an embodiment, the kit comprises a first sterile syringe and a second sterile syringe. The first sterile syringe may comprise an effective amount of a first solution, and the second sterile syringe may comprise an effective amount of a second solution.

Such a kit, as described above, may be tailored to the treatment of particular sizes and types of nerve injuries. Using a kit as described herein may reduce the time necessary for both preparation and treatment of the nerve injury, may improve surgical technique through increased ease of use, and may generally improve the efficiency and efficacy of the nerve repair process.

EXAMPLES

Example 1: Prototype 1

We designed and developed a prototype of the device described herein for the smallest nerve type, the human digital nerve (from about 2 mm to about 2.5 mm in diameter) due to the more technical and engineering challenges of the small size. The prototype was designed as a single-use surgical device employed during the surgical repair of peripheral nerves. We employed rapid prototyping using a three-dimensional (3D) model from a computer-aided design (CAD) and 3D printing to fabricate devices. Prototypes were evaluated for their fit, form, and function by conducting bench tests with model nerves and excised nerves.

Figure 14A:
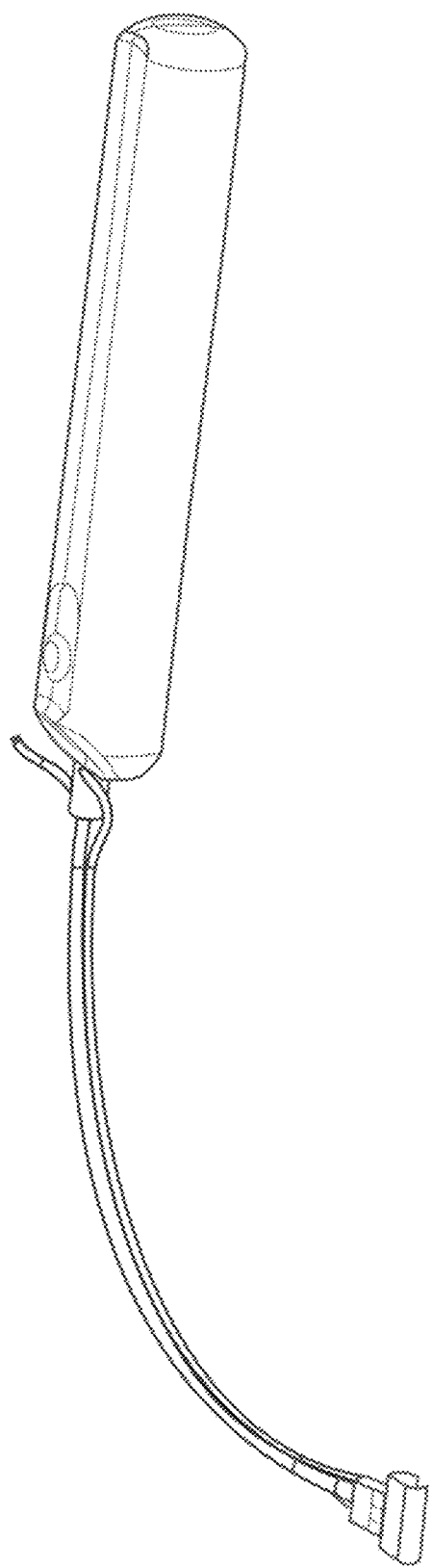
FIG. 14A illustrates an embodiment of a device wherein a handle is configured to open and close an enclosure by sliding at least one of the first portion and the second portion of the enclosure, in accordance with the instant disclosure.
Figure 14B:
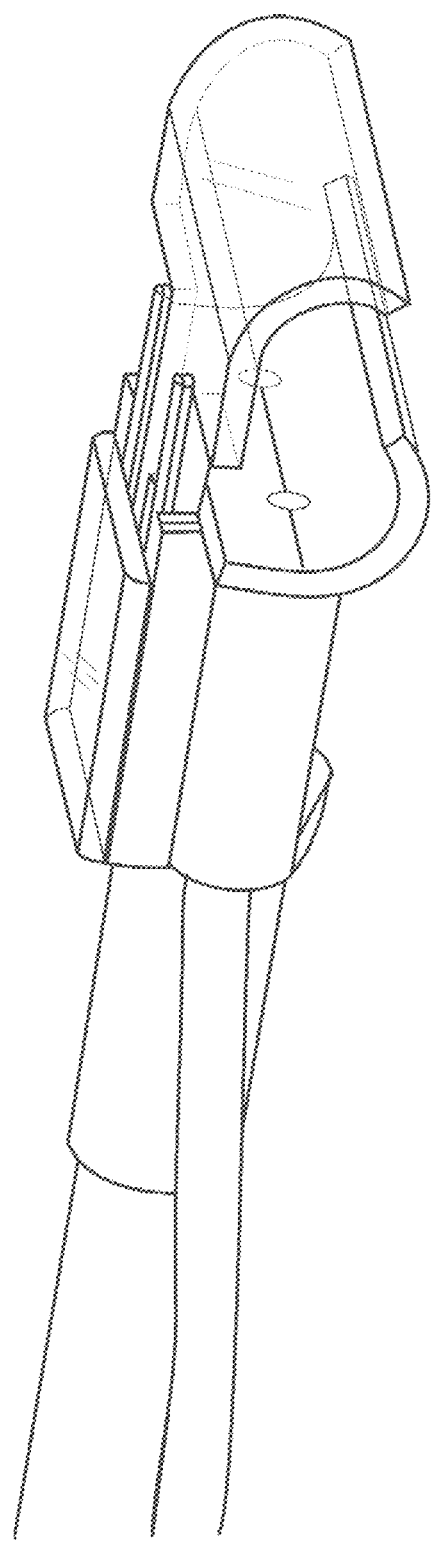
FIG. 14B illustrates an alternative view of an embodiment of a device wherein a handle is configured to open and close an enclosure by sliding at least one of the first portion and the second portion of the enclosure, in accordance with the instant disclosure.

FIG. 14 A and FIG. 14B illustrate a first prototype of a device as described herein ("Prototype 1"). As described herein, the Prototype 1 device has a cylindrical enclosure for isolating the nerve and delivering solutions contained to the injury site. The bottom part of the enclosure is fixed to capture and secure the nerve, while the top part is moveable to open and close the enclosure. The enclosure also has an inlet for delivering the solutions and an outlet for evacuating the solutions. The inlet and outlet are connected to tubing with luer-lock ports for easy connection to syringes. A cylindrical enclosure, compared to the spherical enclosure in the initial proposed design, offers a lower profile requiring less space around the nerve. The cylindrical enclosure is designed to be transparent for visualization of the nerve. The enclosure has transparent hard outer shell with a transparent soft silicone lining at the interfaces and at the nerve openings. The silicone lining is designed to seal the two parts of the enclosure to prevent leaking without causing damage to the nerve. Additionally, by sealing the enclosure, slight pressurization can be achieved which may facilitate penetration of a solution into the nerve bundle to reach the individual axons.

Prototype 1 includes a remote handle connected to the enclosure by a thin, flexible shaft, which reduces nerve damage and is user-friendly. The handle is used to control the opening and closing of the enclosure. Movements of the handle are independent of the enclosure, allowing a surgeon to put the handle down after closing the enclosure around the nerve. One advantage to this design is the low profile, minimizing the material at the repair site and allowing access to deeper nerves. Additionally, this design is easier to use because the handle can be placed down without disrupting the nerve to operate the syringes.

Prototype 1 has a sliding enclosure where the top part slides forward to open and back to close, as illustrated in FIG. 14B. The fixed second portion of the enclosure is used to capture the nerve and then hold it securely while the first portion of the enclosure is closed. The first portion of the enclosure is attached to a rod, placed inside the shaft, for remotely controlling the movement via a handle. A sliding knob on the handle is used to control the movement of the enclosure. This sliding knob, as opposed to a simple button, provides finer control over the extent of closure and the speed of moving the first portion of the enclosure. The dispensing channel and evacuation channel are both located at the second portion of the enclosure, near the back wall.

Prototype 1 and Prototype 2 (described in Example 2 below) were produced by a combination of 3D printing and custom off-the-shelf (COTS) materials. The enclosures comprise polypropylene (PP) parts produced by Stereolithography (SLA) 3D printing. The handles comprise acrylonitrile butadiene styrene (ABS) parts made by Fused Deposition Molding (FDM) 3D printing. The dispensing channel and evacuating channel comprise ethylene vinyl acetate (EVA) tubing (ID 0.02", OD 0.06") connected to luer lock adapters. This small tubing size was selected to reduce waste of the pharmaceutical agents. To connect to the remote handle, the shaft comprises ethylene tetrafluoroethylene (ETFE) tubing (ID 0.093", OD ⅛").

In Prototype 1, three semi-transparent PP parts of the enclosure were assembled by snapping the pieces together, and the pieces were sanded so that the enclosure could slide open and closed smoothly. A thin silicone lining was applied to the top and bottom of the enclosure at the interface of the first portion and the second portion using room temperature vulcanization (RTV) silicone coating. On the sides of enclosure at the nerve openings, a thicker layer of RTV silicone was used. An ABS rod was attached to first portion of the enclosure and placed inside the shaft ETFE tubing to attach to the sliding control knob in the handle. The shaft is ~7 cm in length, which was shortened based on surgeons' feedback.

Additional prototypes include multiple different sizes of the nerve repair device to be used with a variety of nerves from the smallest (digital nerve, 2 mm) to the largest (sciatic nerves, about 20 mm) by scaling the enclosure and the clamp sizes.

The device described herein may be made of transparent plastic to allow for visualization of the nerve during each step of the surgical repair procedure. For feasibility and working prototypes, semi-transparent materials, such as polypropylene or polycarbonate for SLA printed parts, for the enclosure and nerve clamps, may be used. Materials for each part may be selected based on the desired material properties, such as flexibility, strength, etc. Soft, flexible silicone may be used as the material in direct contact with the nerve to prevent damage, and RTV silicone may be manually applied. Medical-grade materials that are amenable to SLA and FDM may also be used. For SLA printed parts, biocompatible polycarbonate-like plastic, such as VISIJET SL Clear (3D Systems), is transparent and meets the United States Pharmacopeia (USP) Class VI. For FDM printed parts, engineering thermoplastics, such as acrylonitrile butadiene styrene-M30i (ABS-M30i) and polycarbonate-ISO (PC-ISO), are biocompatible, complying with USP Class VI and ISO 10993, and gamma and ethylene oxide sterilizable. A medical grade silicone may be used for the silicone linings. For large-scale manufacturing, medical-grade materials amendable to vanous manufacturing processes, such as medical-grade polyoxymethylene (POM) and polyether ether ketone (PEEK) for injection molding, may be used. The entire enclosure may also comprise a flexible material, such as silicone, which requires custom molding processes. Any biocompatibility and cytotoxicity concerns may be mitigated by meeting the biocompatibility requirements set forth by the ISO 10993 series of testing.

Example 2: Prototype 2

Figure 15A:
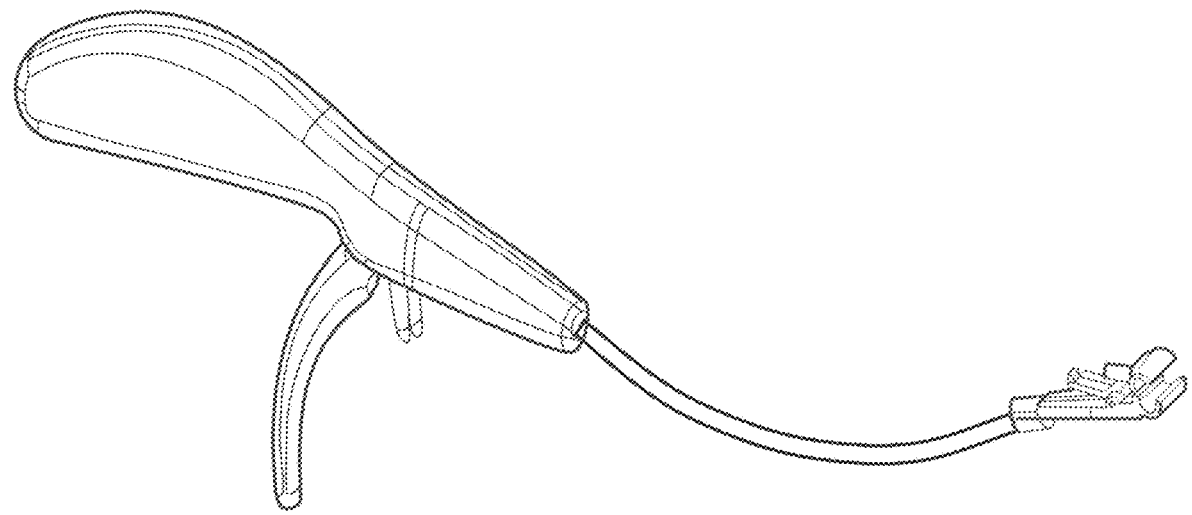
FIG. 15A illustrates an embodiment of a device wherein a handle comprises a hinge mechanism configured to open and close an enclosure in accordance with the instant disclosure.
Figure 15B:
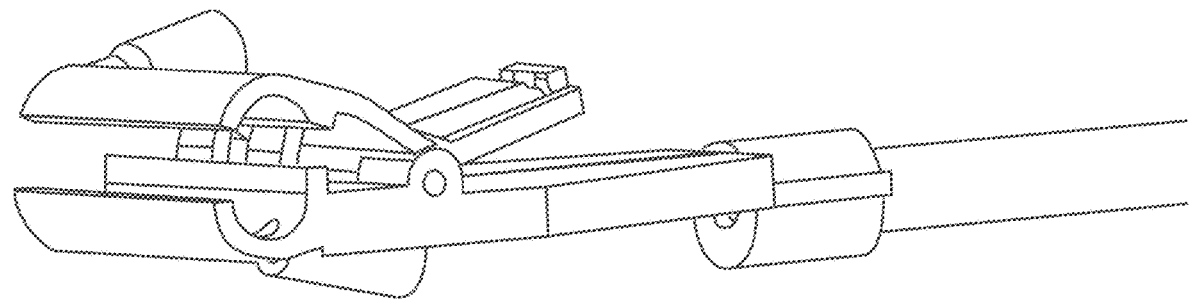
FIG. 15B illustrates an alternative view of an embodiment of a device wherein a handle comprises a hinge mechanism configured to open and close an enclosure in accordance with the instant disclosure.

FIG. 15A and FIG. 15B illustrate a second prototype of a device as described herein ("Prototype 2"), which was made in a manner similar to that of Prototype 1 in Example 1 above. As described herein, the Prototype 2 device has a cylindrical enclosure for isolating the nerve and delivering solutions contained to the injury site. The bottom part of the enclosure is fixed to capture and secure the nerve, while the top part is moveable to open and close the enclosure. The enclosure also has an inlet for delivering the solutions and an outlet for evacuating the solutions. The inlet and outlet are connected to tubing with luer-lock ports for easy connection to syringes. A cylindrical enclosure, compared to the spherical enclosure in the initial proposed design, offers a lower profile requiring less space around the nerve. The cylindrical enclosure is designed to be transparent for visualization of the nerve. The enclosure has transparent hard outer shell with a transparent soft silicone lining at the interfaces and at the nerve openings. The silicone lining is designed to seal the two parts of the enclosure to prevent leaking without causing damage to the nerve. Additionally, by sealing the enclosure, slight pressurization can be achieved which may facilitate penetration of a solution into the nerve bundle to reach the individual axons.

Prototype 2 has a hinge enclosure, which is compatible with a remote handle and thin shaft, as shown in FIG. 15A and FIG. 15B. The moveable first portion of the enclosure hinges to open and close, and a single monofilament connects to the backside of the first portion of the enclosure in order to control the movement remotely. Using the monofilament connected to a remote handle to open and close the enclosure allows for finer movements compared to manually depressing a lever on the top of the enclosure. The shaft is connected to the handle and the monofilament is attached to a trigger in the handle. The advantage of this design is that if the monofilament or the handle fails, the enclosure can still be manually opened and closed. The dispensing channel is located on the second portion of the enclosure and the evacuating channel is located on the first portion of the enclosure to facilitate the circulation of solutions and the removal of any air bubbles. The device is automatically in the closed position due to the wire torsion spring, ensuring the enclosure remains closed when the solutions are delivered. In the opened position, the enclosure has a safety feature that facilitates the correct positioning of the nerve in the bottom part of the enclosure. This safety feature is a wall on the backside of the enclosure that prevents the nerve from being pinched.

The components of Prototype 2 were created as described above with respect to Prototype 1. To assemble the enclosure for Prototype 2, a single pin was used at the hinge axis to attach the two semi-transparent PP parts, and a wire torsion spring was placed as the hinge axis. The spring was appropriately sized so that the enclosure was automatically in the closed position with the tension adjusted to prevent enclosure from snapping closed. RTV silicone was used to thinly line the interfaces of the first and second portions of the enclosure and to thickly coat the sides of the enclosure at the nerve openings. A monofilament was attached to the top of the enclosure to connect the trigger in the handle. A smaller ETFE tubing (ID 0.02", OD 0.06") with the monofilament inside were placed inside the larger shaft tubing. The shaft is ~7 cm in length, which was shortened based on surgeons' feedback. The materials and safety considerations described in Example 1 above with respect to Prototype 1 also apply to Prototype 2.

Example 3: Prototype 3

Figure 16A:
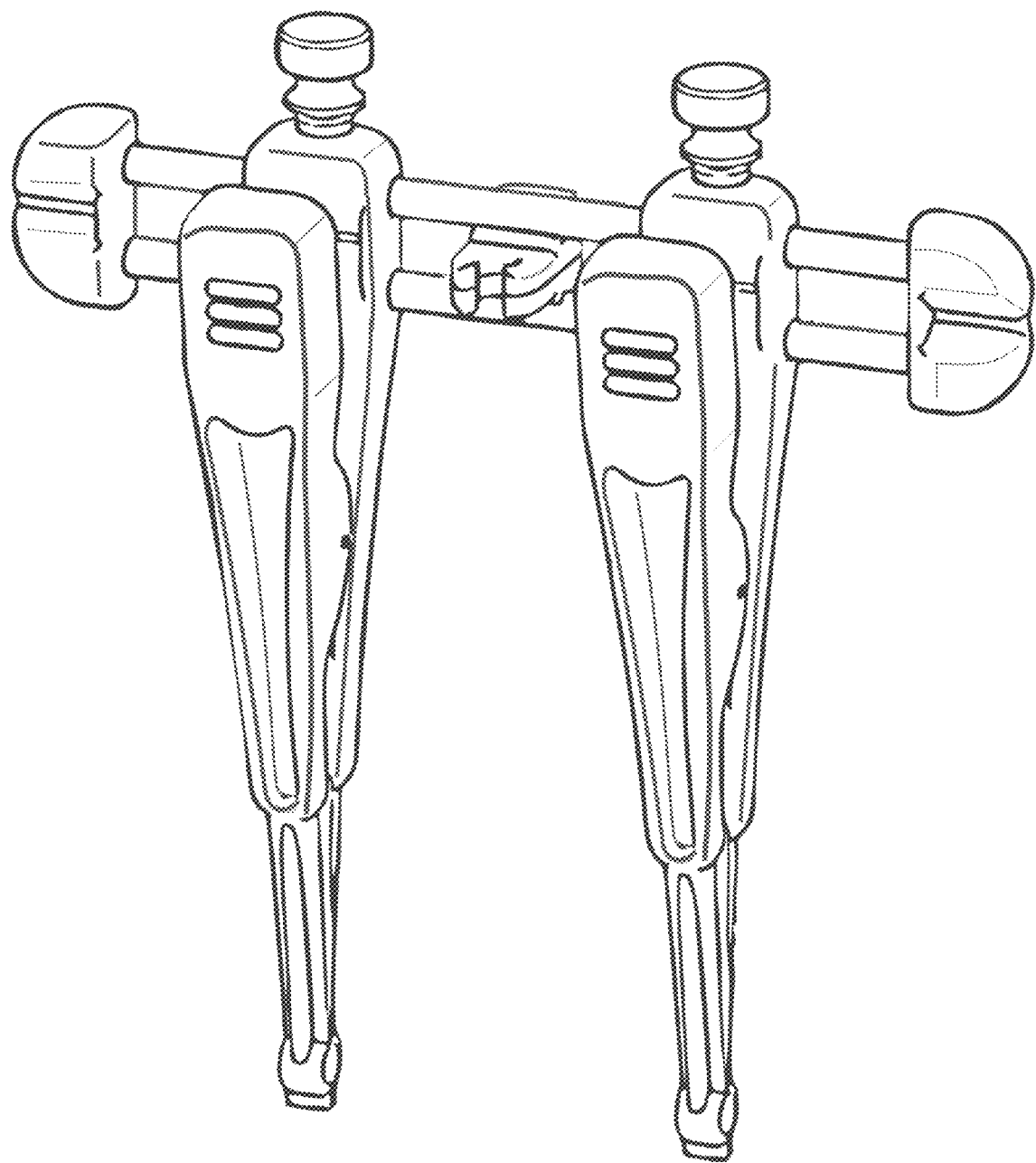
FIG. 16A illustrates a front view of an embodiment of a device having a bar, a first clamp, a second clamp, a mating feature configured to engage with a shaft, and a locking mechanism in accordance with the instant disclosure.
Figure 16B:
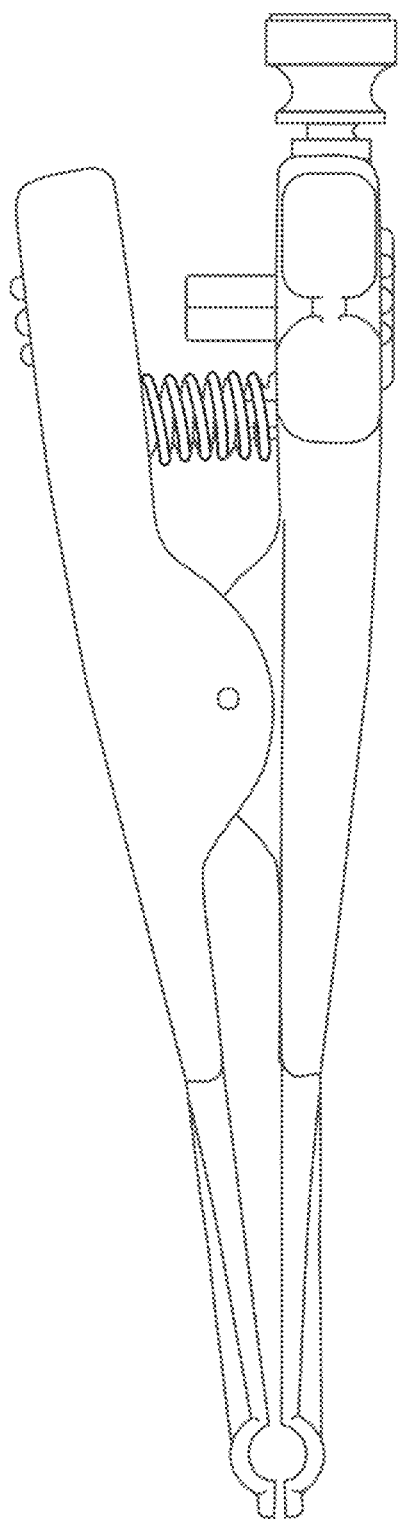
FIG. 16B illustrates a side view of an embodiment of a device having a bar, a first clamp, a second clamp, a mating feature configured to engage with a shaft, and a locking mechanism in accordance with the instant disclosure.

FIG. 16A and FIG. 16B illustrate front and side views, respectively, of a prototype of a device having a bar, a first clamp, a second clamp, a mating feature configured to engage with a shaft, and a locking mechanism in accordance with the instant disclosure. In one embodiment, the first clamp is fixedly engaged with the bar, while the second clamp is slideably engaged with the bar. This arrangement may, in some instances, favor one handedness of user (for example, a right-handed user) over another. In the prototype illustrated in FIG. 16A and FIG. 16B, both clamps are slideably engaged with the bar so that the orientation is not biased to the handedness of the user. The locking mechanism is placed on top of the slideably engaged clamps to allow the user to easily unlock a clamp, adjust its position, and then lock the position along the bar. A mating feature, such as a U- or a clip, may be used to attach the shaft and the enclosure to the bar. The shaft can slide along the bar parallel to the clamps, and the shaft can also to slide back and forth for easy application to a nerve when needed. The clamps may include structural ribbing to increase the mechanical strength and prevent bending. The clamps may also each have about a 3.5 mm width at the top for ease of use. The clamps may include have a hinge for manually opening and closing, and/or a spring to automatically keep the clamp in the closed position, as illustrated in FIG. 16B. The hinge may include two flanges or four flanges. Four flanges may be included to ensure proper alignment, especially of the circular distal ends of the clamps.

Figure 20A:
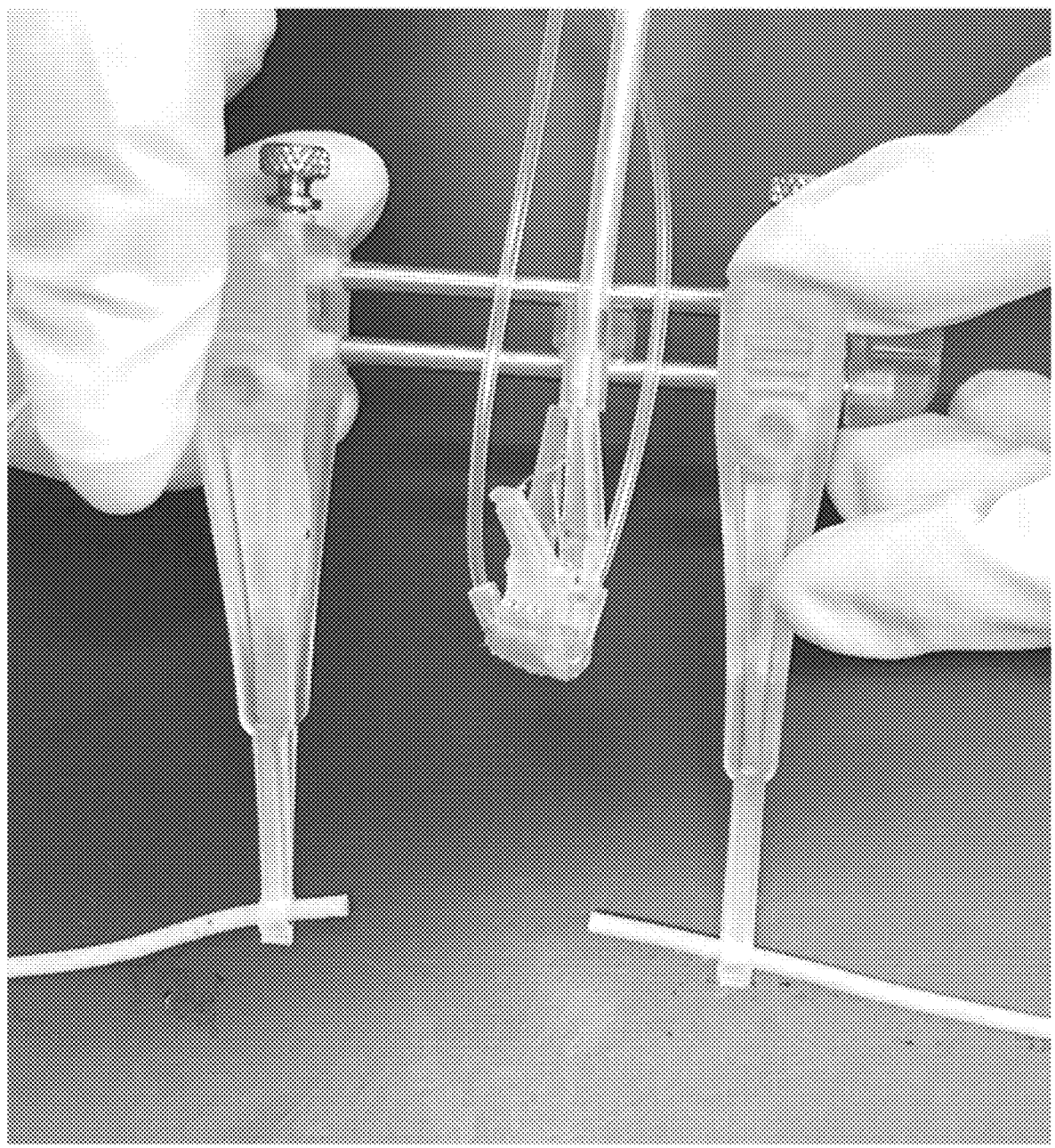
FIG. 20A illustrates an embodiment of the step of engaging a distal end of a first clamp with a first portion of a severed nerve, and engaging a distal end of a second clamp with a second portion of the severed nerve, in accordance with the instant disclosure.
Figure 20B:
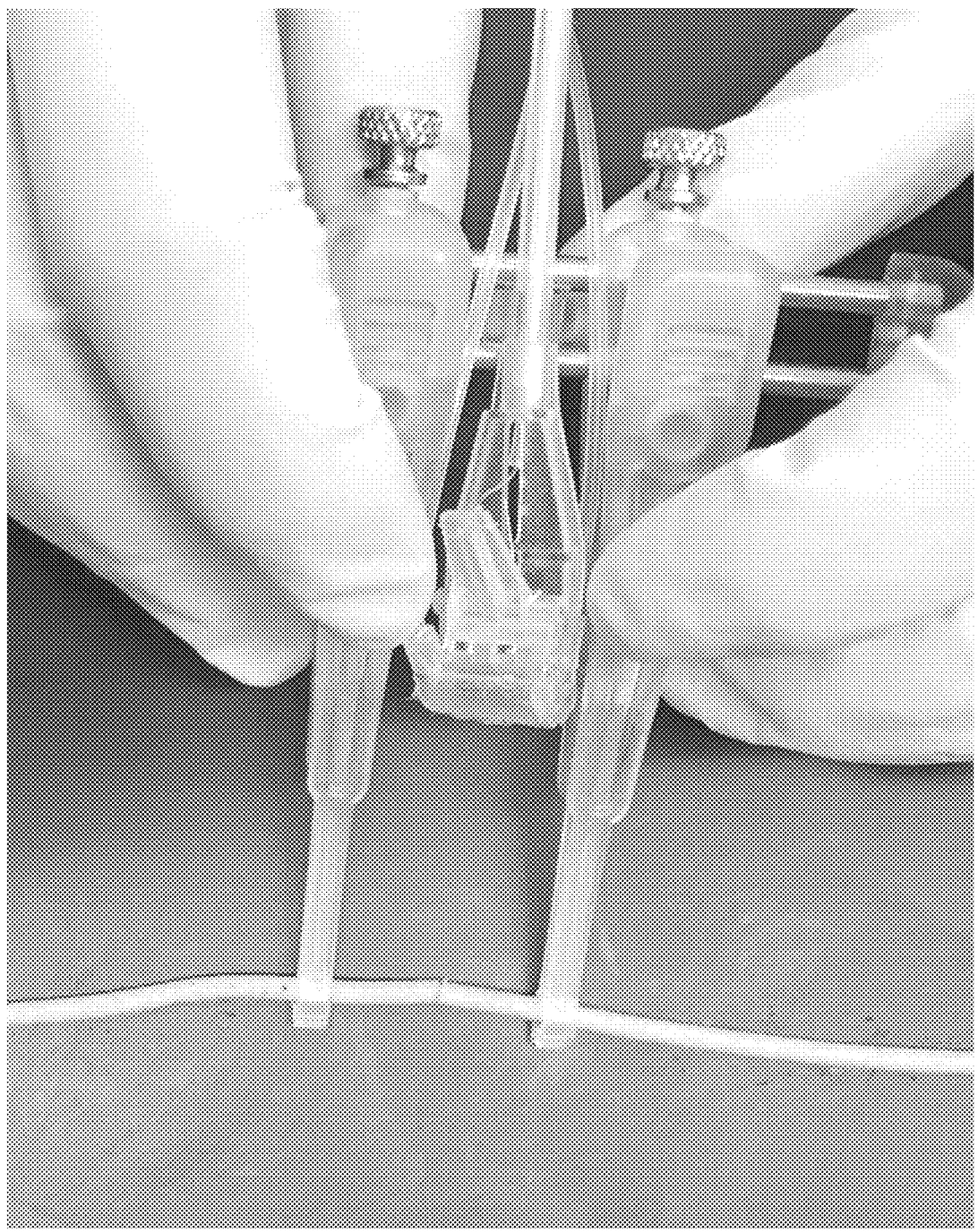
FIG. 20B illustrates an embodiment of the step of sliding the first clamp, the second clamp, or a combination thereof, along a bar to position the first portion of the severed nerve substantially adjacent to the second portion of the severed nerve to form a nerve repair site, in accordance with the instant disclosure.
Figure 20C:
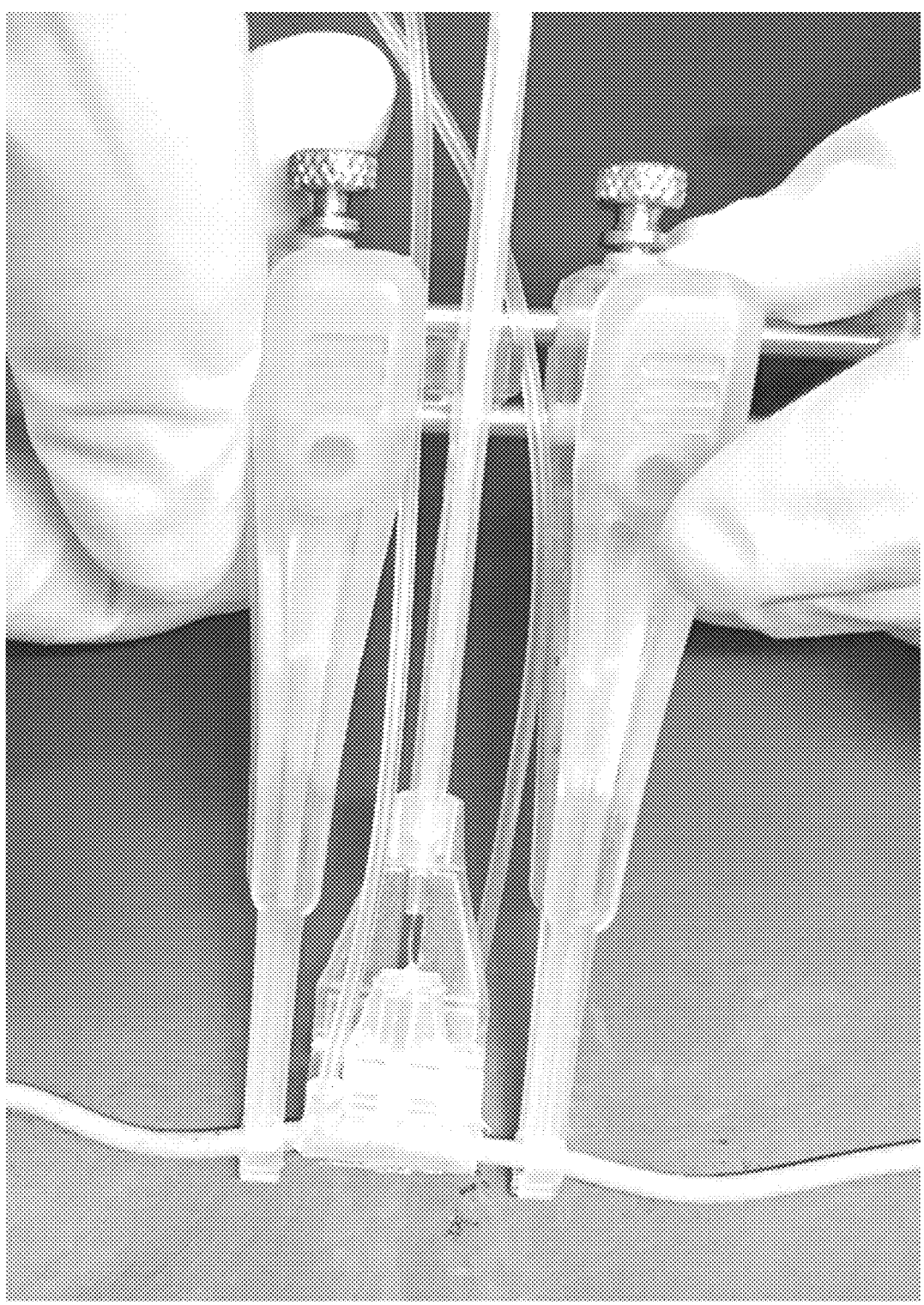
FIG. 20C illustrates an embodiment of the step of closing an enclosure around the nerve repair site, such that the nerve repair site occupies the bore of the enclosure, in accordance with the instant disclosure.

The prototype device shown in FIG. 16A and FIG. 16B was tested using a model nerve (wet spaghetti), as illustrated in FIG. 20A, FIG. 20B, and FIG. 20C, according to a method disclosed herein. FIG. 20A shows an embodiment of the step of engaging a distal end of a first clamp with a first portion of a severed nerve, and engaging a distal end of a second clamp with a second portion of the severed nerve, in accordance with the present disclosure. FIG. 20B shows an embodiment of the step of sliding the first clamp, the second clamp, or a combination thereof, along a bar to position the first portion of the severed nerve substantially adjacent to the second portion of the severed nerve to form a nerve repair site. FIG. 20C shows an embodiment of the step of closing an enclosure around the nerve repair site, such that the nerve repair site occupies the bore of the enclosure, in accordance with the present disclosure. This benchtop testing demonstrated that the clamps can be used to hold and bring two nerve ends together. It also demonstrated that the device can hold the two ends of a nerve and appropriately apply the enclosure to the nerve.

Example 4: In Vitro Testing with Wet Spaghetti

Wet spaghetti (angel hair) was used as a model nerve for in vitro testing, based on texture and size. We evaluated the device as described herein in use, specifically assessing ease of use, handling of the nerve, and delivery of solutions. After securing the nerve in the enclosure, the handle had to be placed down to operate the syringes. When placing the remote handle down, the enclosure did not move or disturb the nerve. Both the sliding and hinge designs for the enclosure were easy to use when capturing and securing the nerve. To capture the nerve, the enclosure of the device was opened, and the nerve was scooped with the bottom of the enclosure. The wall in the back of the enclosure for the hinge designs (including Prototype 2) helped prevent the nerve from slipping too deep in the backside of the enclosure. The enclosure was then closed, and the nerve was easily secured. For the sliding enclosure (including Prototype 1), the speed at which the top was closed was a critical factor. If the first portion of the enclosure was closed quickly, the nerve sometimes rolled back and was pinched between the first and second portion of the enclosure. Slowing sliding the first portion of the enclosure back helped maintain the nerve in a safe position in the second portion of the enclosure to avoid pinching.

Figure 17A:
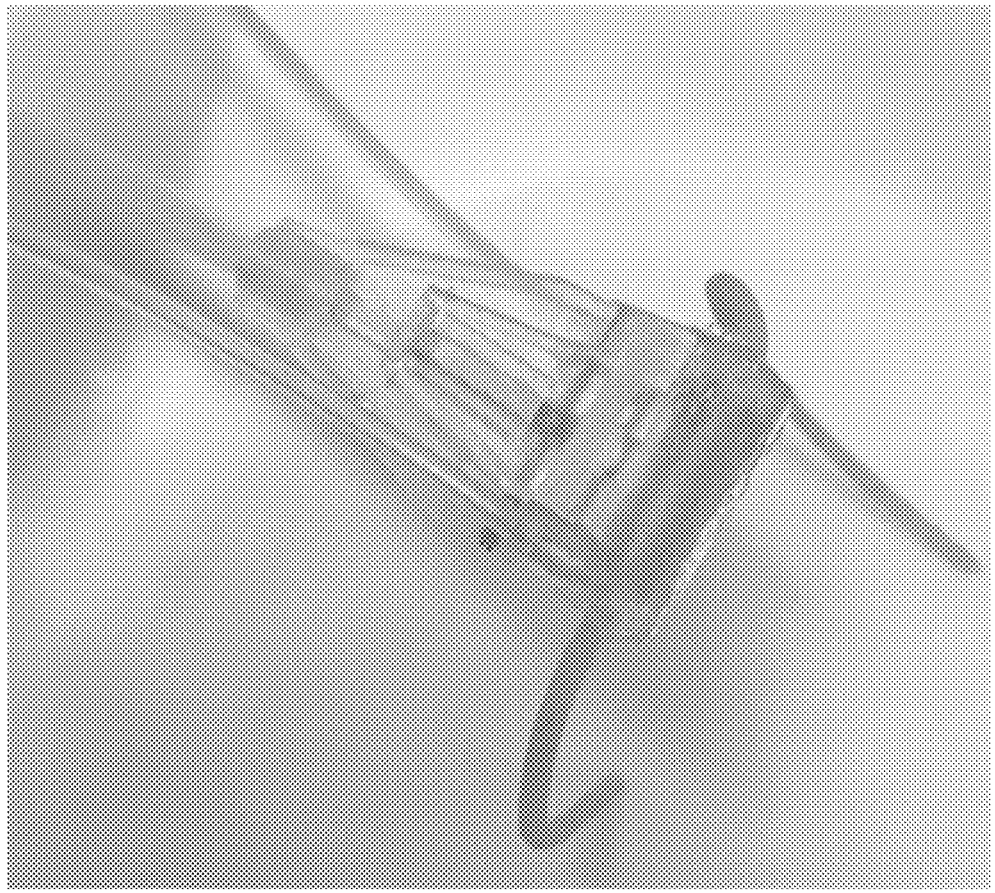
FIG. 17A illustrates in vitro testing of a device and method in accordance with the instant disclosure.
Figure 17B:
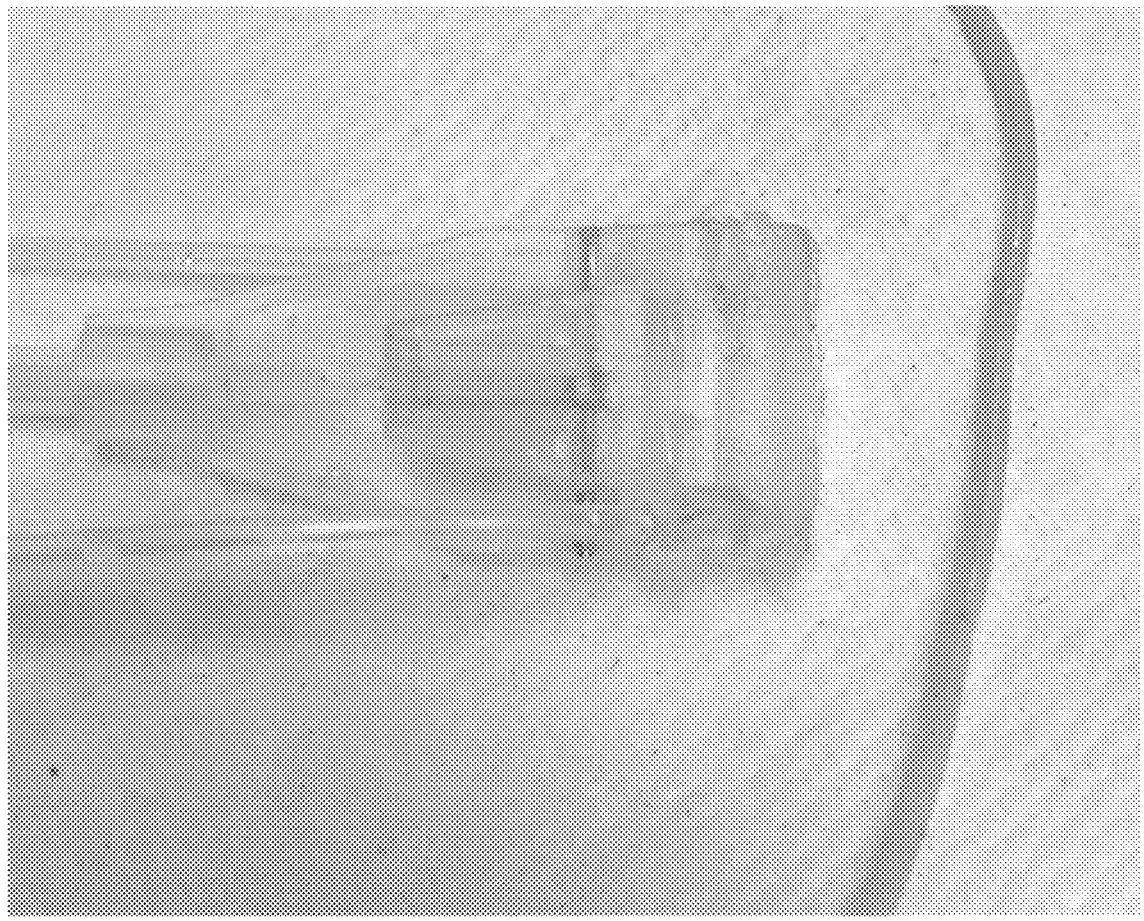
FIG. 17B illustrates an additional view of in vitro testing of a device and method in accordance with the instant disclosure.

The two working prototypes with the silicone linings were further used to evaluate the functions of the delivery system, particularly the coverage of the solutions and the leaks in the enclosure, as well as assess any nerve damage. For demonstration, a 50% (w/v) PEG solution was colored with red food dye to easily observe the delivery of the PEG and to easily detect leaks. The enclosure, with the silicone lining, was well sealed with no leaks. The PEG solution was easily delivered and subsequently evacuated from the enclosure, as shown in FIG. 17A. After removing the model nerve (spaghetti), the section of the spaghetti in the enclosure turned red, as shown in FIG. 17B, indicating full PEG coverage. Together, FIG. 17A and FIG. 17B illustrate the delivery and application of a solution to the portion of the model nerve that is isolated in the enclosure. We also visually inspected the spaghetti for any damage, looking specifically for pinching where the sides of the enclosure at the nerve openings made direct contact with the nerve. In initial prototypes, the sides were made of hard plastic, some with a thin silicone lining, that compressed and pinched the nerve. For Prototypes 1 and 2, the thick silicone lining at the nerve openings did not cause any visible damage to the model nerves.

Figure 18:
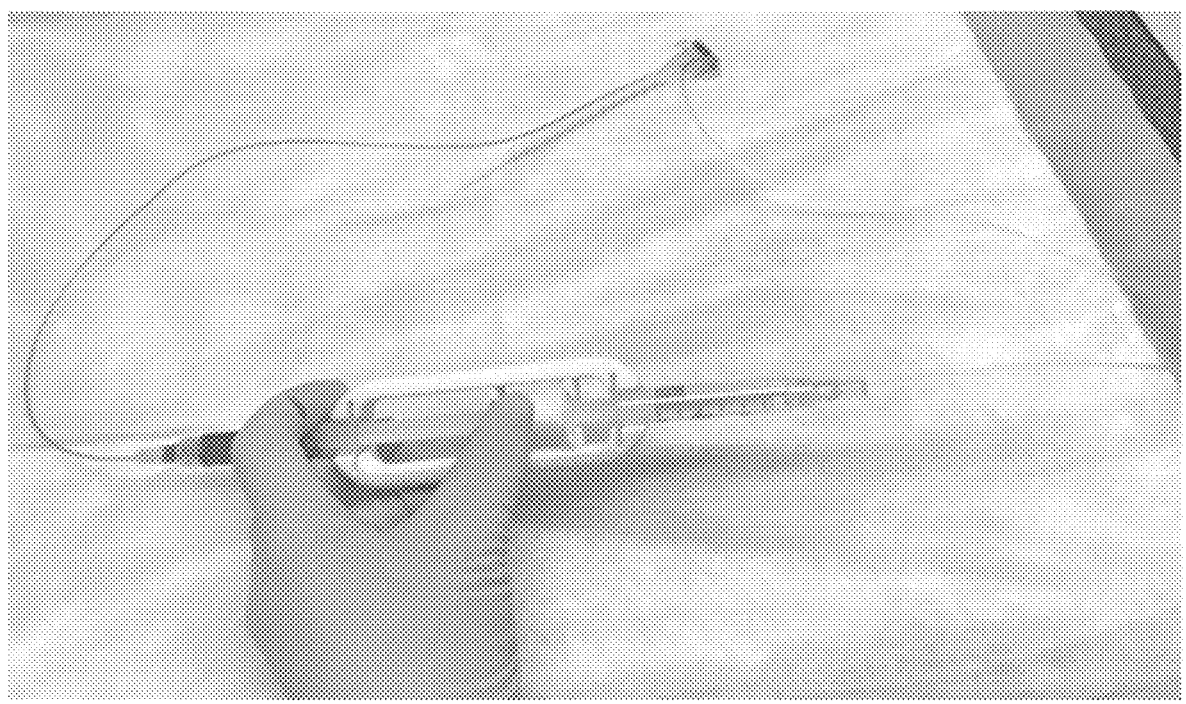
FIG. 18 illustrates an embodiment of a syringe-coordinating tool in accordance with the instant disclosure.

Over-pressurizing the enclosure could damage the nerve. To mitigate this risk, the evacuating channel can be used to suction air using an empty syringe as a pressure relief while dispensing the solution. The two syringes can be manually operated, but coordinating the syringes may be challenging for a single operator. We developed a simple solution to easily coordinate the syringes. A simple syringe-coordinating tool, as illustrated in FIG. 18, fabricated by FDM 3 printing, was designed to dispense one syringe while simultaneously suctioning the other syringe which can facilitate circulating the solution in the enclosure. This syringe-coordinating tool can be easily operated using one hand. In some embodiments, this syringe-coordinating tool may be designed specifically for 3 mL syringes, and rates of dispensing and suctioning may be 1:1. We demonstrated the use of this tool with the delivery device for dispensing and evacuating a solution. The syringe-coordinating tool may also be designed for other rates of dispensing and suctioning, as a well as for other syringe sizes.

Example 5: Ex Vivo Testing with Rat Sciatic Nerves

We evaluated the performance of the device for delivering solutions ex vivo using freshly excised rat sciatic nerves. To mimic the surgical repair with a fusion protocol, the nerve was severed, microsutured, and then the solutions were applied using the device. The factors for device performance included the application of a series of solutions isolated to the nerve without leakage, coverage of the solutions at the repair site, penetration of the solutions into the nerve bundle, and handling of the nerve.

Figure 19A:
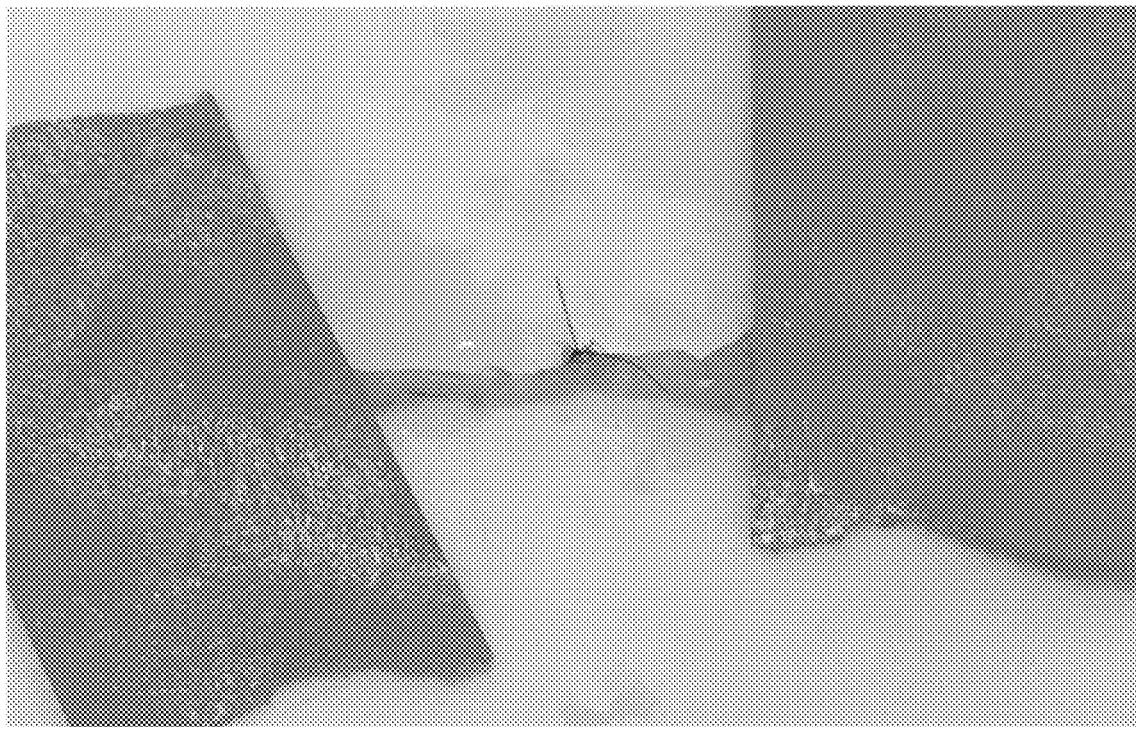
FIG. 19A illustrates a step of repairing a cut-severed nerve using microsutures during ex vivo testing of a device and method in accordance with the instant disclosure.
Figure 19B:
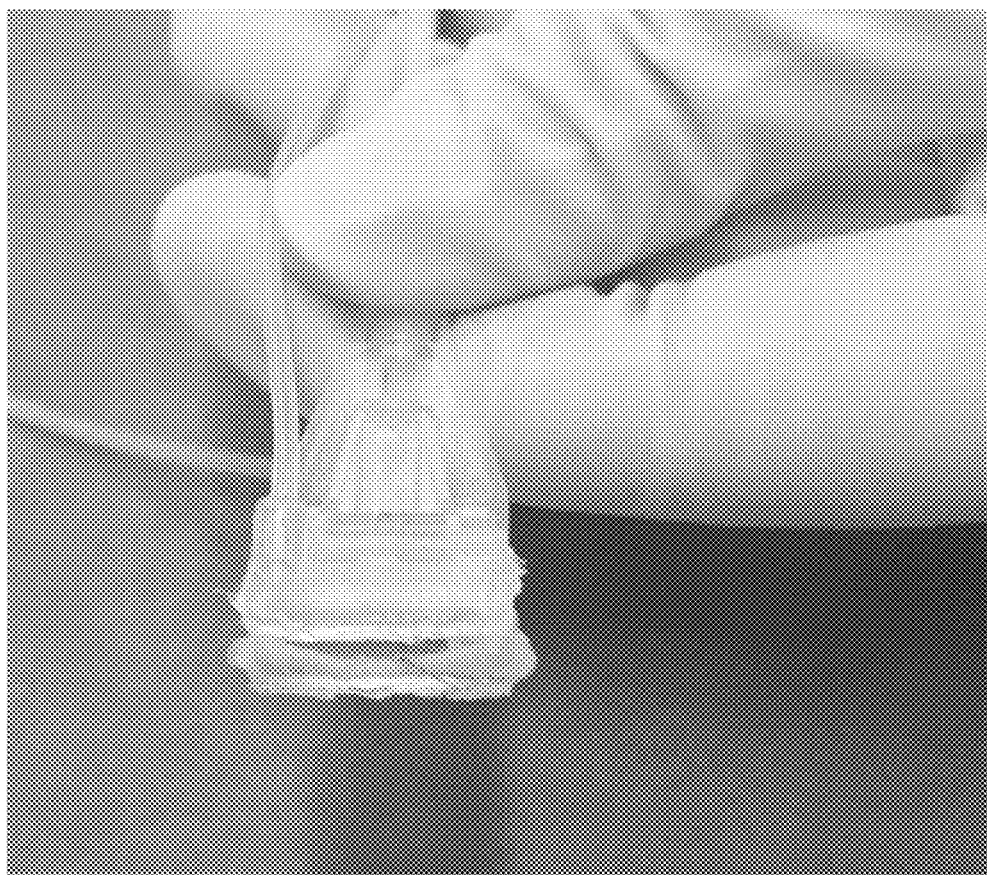
FIG. 19B illustrates a step of capturing a cut-severed nerve during ex vivo testing of a device and method in accordance with the instant disclosure.
Figure 19C:
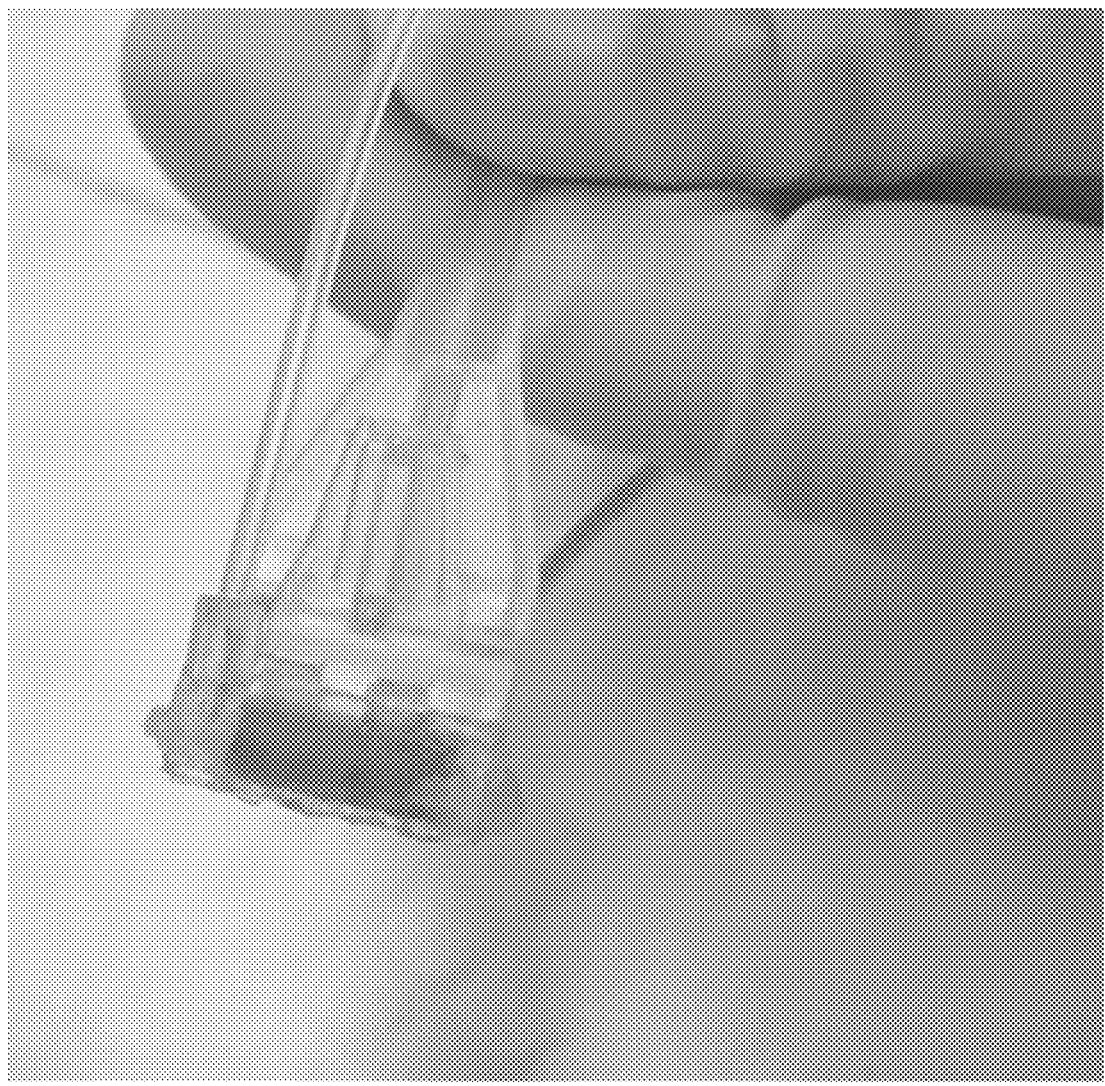
FIG. 19C illustrates the steps of delivering a solution through a dispensing channel to a nerve repair site and removing the solution through an evacuating channel from the nerve repair site during ex vivo testing of a device and method in accordance with the instant disclosure.
Figure 19D:
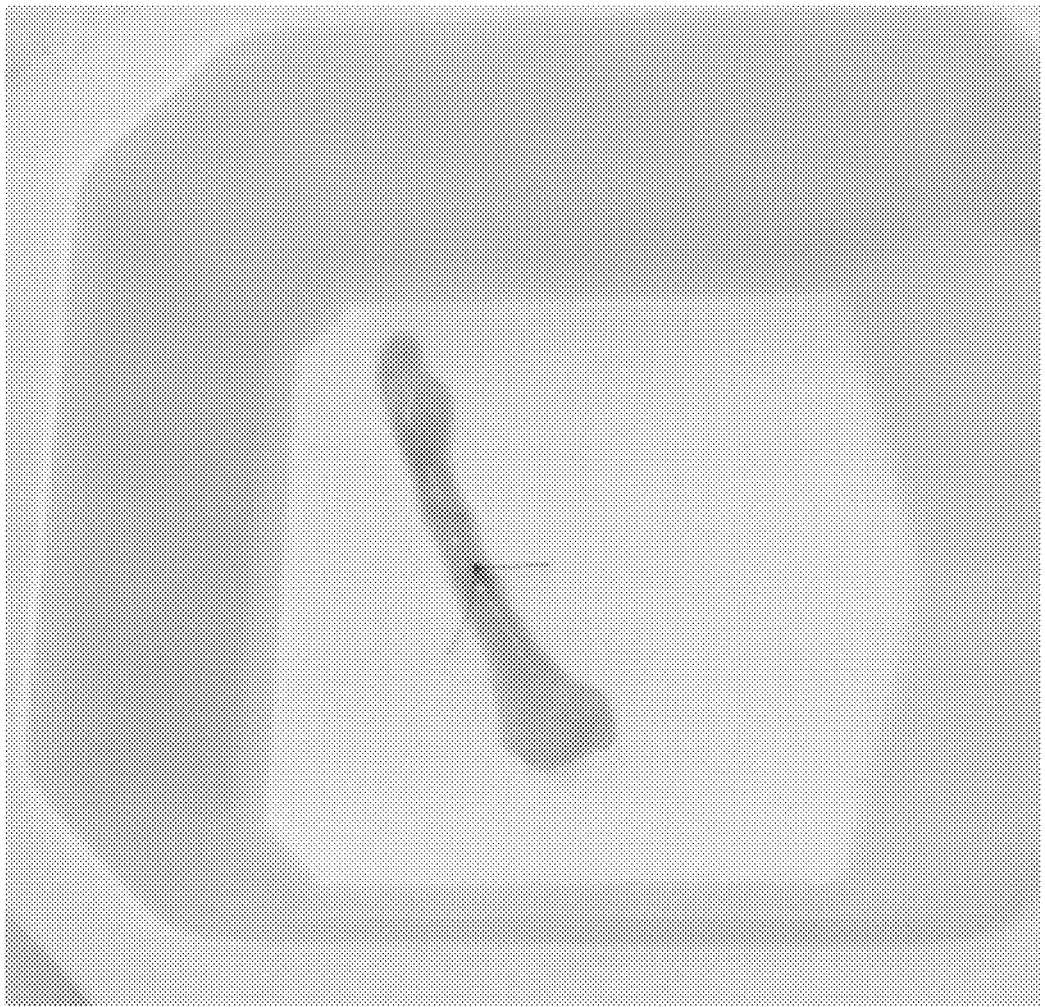
FIG. 19D illustrates an evenly blue-colored nerve section as a result of ex vivo testing of a device and method in accordance with the instant disclosure.
Figure 19E:
FIG. 19E illustrates a microscopic image of an evenly blue-colored nerve section as a result of ex vivo testing of a device and method in accordance with the instant disclosure.
Figure 19F:
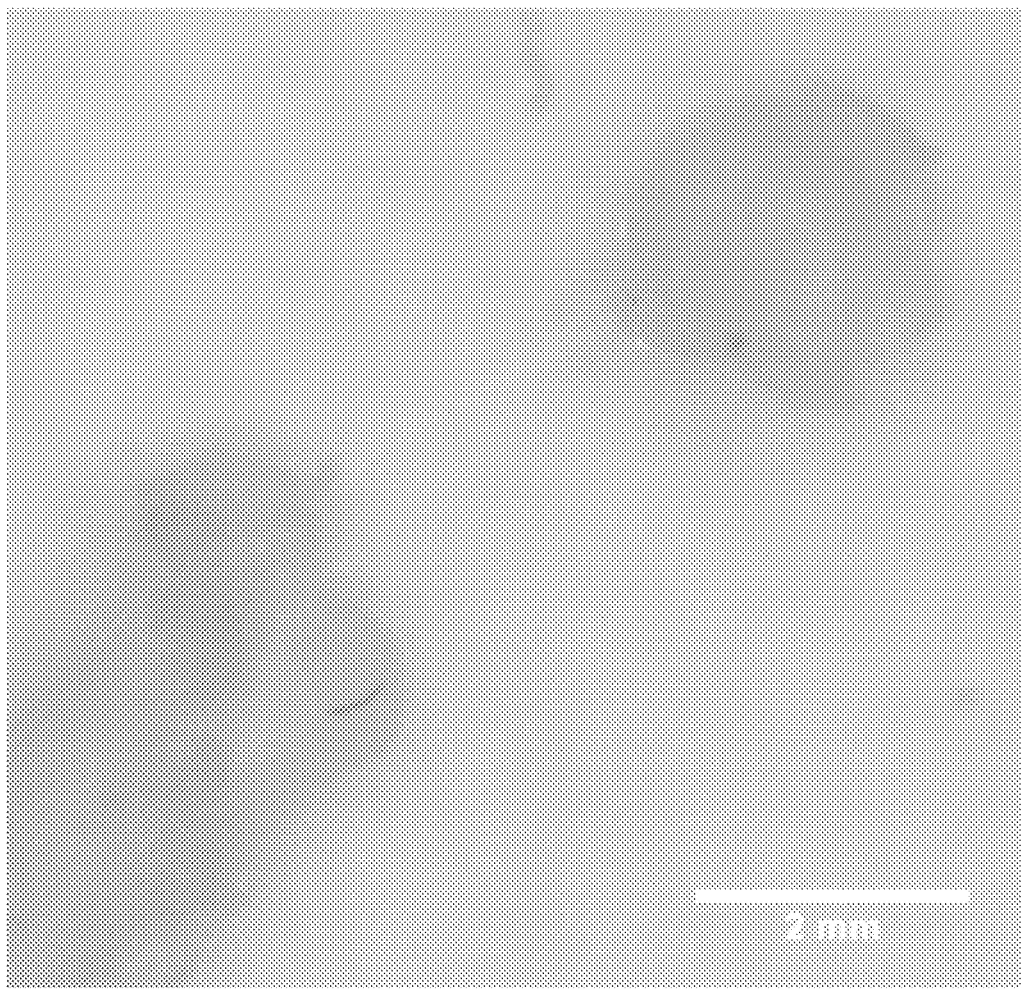
FIG. 19F illustrates a cross-sectional microscopic image of an evenly blue-colored nerve section as a result of ex vivo testing of a device and method in accordance with the instant disclosure.

A cut severance injury was made using a No. 10 blade scalpel, and the injury was repaired using microsutures (Sharpoint size 8-0 Nylon monofilament suture with a 140 µm taper needle, eSutures.com) applied with jeweler forceps under a stereomicroscope. FIG. 19A shows the microsutured nerve repair site. A delivery device as described here was then used to apply fusion solutions. With the enclosure opened, the nerve was securely captured in the second portion of the enclosure, as shown in FIG. 19B. With the enclosure closed, a 50% PEG solution, with ~0.01% methylene blue (PEG+MB) added for visualization, was applied to the nerve for one minute, as shown in FIG. 19C. The PEG solution was evacuated, and a calcium-containing saline (Lactated Ringers buffer) was applied for one minute. As a result, the epineurium of the nerve was dyed blue, showing an even color distribution as shown in FIG. 19D. We used a stereomicroscope (Nikon SMZ100) to further examine the PEG+MB distribution, both externally and internally. Under 0.8× magnification, the epineurium was not evenly dyed, as shown in FIG. 19E, which may be attributed to the uneven structure or some external damage. To observe the penetration of the PEG into the nerve bundle, we cut a cross-section of the nerve at the repair site. Under 1.5× magnification, the blue color was observed in the nerve bundle beyond the epineurium, as shown in FIG. 19F, indicating that the PEG solution delivered with the device penetrated into the nerve bundle.

Example 6: Kit

A kit may contain up to four sterile prefilled syringes with an effective amount of each solution for use in conjunction with the device and method described herein. One purpose of the kit is to provide access to the sterile solutions needed for PEG fusion in hospitals, as well as to provide rapid setup and minimal preparation. In one experiment, we produced the sterile solutions and packaged them individually in syringes using aseptic technique. We used plastic syringes in the kit, since they are robust, reduce the risk of breakage, and are lighter weight than glass vials. Regulatory guidelines were followed to select the syringes to package the individual solutions.

To assemble an easy-to-use kit as described herein, we purchased the required chemicals and solutions. Using aseptic technique in a laminar flow hood, we prepared a 1% (w/w) methylene blue solution in distilled water and sterilized by filtering with an 0.2 µm vacuum filtration unit. We also prepared a 50% (w/v) PEG (3350 kDa) solution in distilled water, stirred overnight to completely dissolve, and then sterilized by filtering with an 0.2 µm vacuum filtration unit.

For packaging the solutions in the kit, we selected all-plastic syringes with luer lock tips (sterile Norm-Jet 3 mL syringes, Air-Tite Products Co., Inc.) that meet the regulatory criteria (FDA registered, CE Mark, ISO 9001 certified, and DEHP-free) and syringe caps (sterile syringe caps, Air-Tite Products Co., Inc.) to cap and seal luer lock syringes. Syringes were filled manually under sterile conditions in a laminar flow hood using aseptic technique. MB and PEG solutions were individually packaged as 1 mL per syringe based on the dose needed for human digital nerves (or rat sciatic nerves).

cGMP should be closely followed to produce sterile solutions using pharmaceutical and USP grade materials for the kits described herein. Sterile calcium-free and calcium-containing saline solutions may be used. All-plastic syringes that meet regulatory requirements and traditional filling processes under sterile conditions may also be used to produce the prefilled syringes for the kit. To minimize degradation by oxidation, oxygen may be purged from the container using argon prior to packaging. To further minimize degradation, packaging that serves as an oxygen barrier and provides protection from light may also be used. Ethylene vinyl alcohol (EVOH) copolymer is a high-performance barrier to oxygen, and EVOH is widely and commonly used in food packaging materials. EVOH is commonly coextruded or laminated as a thin layer between cardboard, foil, or other plastics. Foil packaging offers protection from light. For packaging the kit, EVOH/foil and/or EVOH/cardboard packaging may be used.

Various techniques to manufacture prefilled syringes including bubble-free filling, which uses online vacuum filling and online vacuum stopping, to reduce the head space in the syringe and form-fill-seal technology using aseptic manufacturing and automatic sterilization, may also be used. In the latter method, a polymeric material is formed and sealed inline to a container of choice, while the container is being filled, requiring only one piece of automated machinery and short processing time (six seconds or less). All materials and processes for large-scale manufacturing, including producing sterilize solutions, individually packaging sterile solution in syringes, and packaging of the entire kit, may be used.

While the present disclosure has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicant's general inventive concept.

The invention claimed is:

1. A device comprising:
a shaft comprising a dispensing channel and an evacuating channel, the shaft having a proximal end and a distal end;
an enclosure attached to the distal end of the shaft, the enclosure having a first portion and a second portion, wherein the first portion and the second portion form a bore when the enclosure is closed, wherein the first portion of the enclosure and the second portion each comprise a flexible material configured to seal the enclosure around a lumen, and wherein the lumen is a nerve repair site; and
a handle attached to the proximal end of the shaft, wherein the handle is configured to open and close the enclosure.

2. The device of claim 1, wherein the dispensing channel is configured to deliver a solution to the bore of the enclosure, and wherein the evacuating channel is configured to remove the solution from the bore of the enclosure.

3. The device of claim 2, wherein the solution comprises a membrane fusogen, poly(ethylene glycol), calcium, methylene blue, hypotonic saline, isotonic saline, nerve growth factor, glial cell-derived neurotropic factor, neurotrophin 3, brain-derived neurotrophic factor, insulin-like growth factor, platelet-derived growth factors, ciliary neurotrophic factors, fibroblast growth factor, erythropoietin, tacrolimus, cyclosporine, a nerve growth stimulation agent, air, a gas, a fluid, an antioxidant, a pharmaceutical, a biologic, or a combination thereof.

4. The device of claim 1, wherein the dispensing channel and the evacuating channel are attached to an external portion of the shaft, contained within the shaft, or concentric.

5. The device of claim 1, wherein the proximal end of the dispensing channel further comprises a reservoir.

6. The device of claim 1, further comprising a third channel having a mechanism configured to control the opening and closing of the enclosure.

7. The device of claim 1, wherein the enclosure further comprises at least one port around the bore, a pressure relief mechanism, or a combination thereof.

8. The device of claim 1, wherein the first portion of the enclosure and the second portion of the enclosure are connected by a mechanism selected from the group consisting of a hinge, a flexure bearing, and a clip.

9. The device of claim 1, wherein the handle is configured to mechanically open and close the enclosure by an action selected from the group consisting of using a spring, sliding at least one of the first portion and the second portion, and combinations thereof.

10. The device of claim 1, further comprising:
a bar slideably engaged with the shaft;
a first clamp engaged with the bar and a second clamp engaged with the bar, wherein the shaft is positioned between the first clamp and the second clamp; and
a locking mechanism configured to fix the position of the first clamp, the second clamp, or a combination thereof, along the bar.

11. The device of claim 10, wherein each of the first clamp and the second clamp has a distal end configured to grip at least a portion of the lumen, and wherein each of the distal end of the first clamp and the distal end of the second clamp are configured to prevent compression of the lumen.

12. The device of claim 10, wherein the first clamp is fixedly or slideably engaged with the bar, the second clamp is fixedly or slideably engaged with the bar, and the locking mechanism is configured to fix the position of at least one of the first clamp and the second clamp along the bar.

13. A method for delivering a solution to a nerve repair site, the method comprising:
   obtaining a device comprising:
      a shaft comprising a dispensing channel and an evacuating channel, the shaft having a proximal end and a distal end;
      an enclosure attached to the distal end of the shaft, the enclosure having a first portion and a second portion, wherein the first portion and the second portion form a bore when the enclosure is closed, wherein the first portion of the enclosure and the second portion of the enclosure each comprise a flexible material configured to seal the enclosure around a lumen, and wherein the lumen is a nerve repair site; and
      a handle attached to the proximal end of the shaft, wherein the handle is configured to open and close the enclosure;
   closing the enclosure around the nerve repair site, such that the nerve repair site occupies the bore of the enclosure;
   delivering a solution through the dispensing channel to the nerve repair site;
   removing the solution through the evacuating channel from the nerve repair site; and
   opening the enclosure to remove the enclosure from the nerve repair site.

14. The method of claim 13, further comprising pressurizing the enclosure, wherein pressurizing the enclosure comprises delivering the solution to the enclosure via the dispensing channel, and wherein delivering the solution to the enclosure via the dispensing channel further comprises using an external pressure source.

15. The method of claim 13, wherein closing the enclosure around the nerve repair site comprises sliding the first portion of the enclosure to meet the second portion of the enclosure.

16. The method of claim 13, wherein closing the enclosure around the nerve repair site comprises activating a spring mechanism to bring the first portion of the enclosure and the second portion of the enclosure together.

17. The method of claim 13, wherein closing the enclosure around the nerve repair site further comprises engaging a clip to lock the first portion of the enclosure and the second portion of the enclosure around the nerve repair site.

18. A method for repairing a severed nerve, the method comprising:
   obtaining a device comprising:
      a bar;
      a shaft slideably engaged with the bar, the shaft having a proximal end and a distal end;
      an enclosure attached to the distal end of the shaft, the enclosure having a dispensing channel, an evacuating channel, a first portion, and a second portion, wherein the first portion and the second portion form a bore when the enclosure is closed;
      a handle attached to the proximal end of the shaft, wherein the handle is configured to open and close the enclosure;
      a first clamp engaged with the bar and a second clamp engaged with the bar, wherein the shaft is positioned between the first clamp and the second clamp; and
      a locking mechanism configured to fix the position of the first clamp, the second clamp, or a combination thereof, along the bar;
   engaging a distal end of the first clamp with a first portion of the severed nerve;
   engaging a distal end of the second clamp with a second portion of the severed nerve;
   sliding the first clamp, the second clamp, or a combination thereof, along the bar to position the first portion of the severed nerve substantially adjacent to the second portion of the severed nerve to form a nerve repair site;
   engaging the locking mechanism to fix the position of the first clamp, the second clamp, or a combination thereof, along the bar;
   closing the enclosure around the nerve repair site, such that the nerve repair site occupies the bore of the enclosure;
   delivering a solution through the dispensing channel to the nerve repair site;
   removing the solution through the evacuating channel from the nerve repair site;
   opening the enclosure to remove the enclosure from the nerve repair site; and
   releasing the first clamp from the first portion of the severed nerve, and releasing the second clamp from the second portion of the severed nerve.

19. The method of claim 18, further comprising applying one or more microsutures to the nerve repair site before releasing the first clamp from the first portion of the severed nerve, and prior to releasing the second clamp from the second portion of the severed nerve.

* * * * *